(12) United States Patent
Miyamoto et al.

(10) Patent No.: US 9,488,815 B2
(45) Date of Patent: Nov. 8, 2016

(54) PATTERN EVALUATION METHOD AND PATTERN EVALUATION DEVICE

(71) Applicant: Hitachi High-Technologies Corporation, Tokyo (JP)

(72) Inventors: Atsushi Miyamoto, Tokyo (JP); Mayuka Osaki, Tokyo (JP); Maki Kimura, Tokyo (JP); Chie Shishido, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 402 days.

(21) Appl. No.: 14/360,649

(22) PCT Filed: Jan. 30, 2013

(86) PCT No.: PCT/JP2013/051945
§ 371 (c)(1),
(2) Date: May 26, 2014

(87) PCT Pub. No.: WO2013/118613
PCT Pub. Date: Aug. 15, 2013

(65) Prior Publication Data
US 2014/0320627 A1    Oct. 30, 2014

(30) Foreign Application Priority Data
Feb. 8, 2012 (JP) .................. 2012-024657

(51) Int. Cl.
*G02B 21/00* (2006.01)
*G03F 7/20* (2006.01)
*H01J 37/28* (2006.01)
(Continued)

(52) U.S. Cl.
CPC ............. *G02B 21/008* (2013.01); *G01N 23/00* (2013.01); *G03F 7/70633* (2013.01); *H01J 37/28* (2013.01); *H01J 2237/2817* (2013.01); *H01L 21/0337* (2013.01); *H01L 22/12* (2013.01); *H01L 2924/0002* (2013.01)

(58) Field of Classification Search
CPC  G02B 21/008; G01N 23/00; G03F 7/70633; H01J 37/28
USPC .......................................................... 348/80
See application file for complete search history.

(56) References Cited

U.S. PATENT DOCUMENTS 7,684,609 B1 * 3/2010 Toth ....................... G06T 7/001
                                                                  382/141
2006/0263706 A1 * 11/2006 Yim .................... G03F 7/70633
                                                                  430/22
(Continued)

FOREIGN PATENT DOCUMENTS

JP       06-202311 A     7/1994
JP     2007-003212 A     1/2007
(Continued)

*Primary Examiner* — Jeffery Williams
(74) *Attorney, Agent, or Firm* — Miles & Stockbridge P.C.

(57) ABSTRACT

An pattern evaluation method includes a step of estimating imaging deviation allowed to evaluate an overlay position on one or more evaluation point candidates based on pattern layout information, a step of deciding one or more evaluation points from among the evaluation point candidates based on the allowed imaging deviation, a step of deciding an imaging sequence for imaging the selected evaluation point, and a step of evaluating an overlay position between first and second patterns based on an image obtained by imaging the evaluation point according to the imaging sequence.

16 Claims, 16 Drawing Sheets

(51) Int. Cl.
  *G01N 23/00* (2006.01)
  *H01L 21/033* (2006.01)
  *H01L 21/66* (2006.01)

(56) References Cited

U.S. PATENT DOCUMENTS

2006/0284081 A1 12/2006 Miyamoto et al.
2011/0268363 A1 11/2011 Osaki et al.
2012/0106826 A1 5/2012 Toyoda et al.
2012/0267528 A1 10/2012 Sakai et al.

FOREIGN PATENT DOCUMENTS

| | | |
|---|---|---|
| JP | 2010-177500 A | 8/2010 |
| JP | 2011-013022 A | 1/2011 |
| JP | 2011-133378 A | 7/2011 |
| KR | 10 2009 0099413 | 6/2012 |

* cited by examiner (a)

(b)

PATTERN EVALUATION METHOD AND PATTERN EVALUATION DEVICE

TECHNICAL FIELD

A method of effectively inspecting an overlay of circuit patterns formed on a wafer with a high degree of accuracy using a scanning charged particle microscope in a semiconductor device is provided.

BACKGROUND ART

In order to form a circuit pattern on a semiconductor wafer, for example, a method of forming a circuit pattern by coating a semiconductor wafer with a coating material called a resist, placing an exposure mask (reticle) of a circuit pattern on the resist, radiating visible light, ultraviolet light, or electron beams from above, forming the circuit pattern by the resist on the semiconductor wafer by exposing the resist to light and developing the resist, and etching the semiconductor wafer using the circuit pattern of the resist as a mask has been employed.

In a semiconductor manufacturing process, when a circuit pattern is formed on various kinds of thin films formed on multiple layers, overlay accuracy between patterns of upper and lower layers is an important evaluation item of affecting the performance of a semiconductor device. As a method of evaluating an overlay between patterns of upper and lower layers, PTL 1 (JP 6-202311 A) discloses a method of acquiring an optical image of an overlay evaluation-dedicated pattern formed on a wafer in advance and evaluating a deviation amount between respective layers by image analysis.

Further, as a pattern miniaturization technique, double patterning (which is referred to as "DP") of forming patterns on the same layer by different exposure steps and implementing high-density patterns has been put to practical use. A double exposure technique which is one of the DP techniques will be described. First, a resist is coated on a wafer to form a first resist film, and a first pattern by the first exposure is formed by exposing the first resist film to light and developing the first resist film. Then, the first pattern is frozen not to be exposed to light in second exposure. A resist for the second exposure is coated thereon to form a second resist film, and a second pattern between the first patterns is formed by the second exposure. Using this technique, a resist pattern can be formed at a pitch which is half a minimum pitch at which a resist pattern can be formed by single exposure. The DP is disclosed in PTL 2 as well.

As a method of evaluating an overlay between a first pattern and a second pattern in the DP, PTL 2 (JP 2010-177500 A) discloses a method of comparing information of the layout in which the first pattern and the second pattern to be arranged with an image obtained by imaging the patterns based on the information of the layout.

CITATION LIST

Patent Literatures

PTL 1: JP 6-202311 A
PTL 2: JP 2010-177500 A

SUMMARY OF INVENTION

Technical Problem

It is an object of the present invention to provide a method of closely estimating an overlay deviation between patterns of upper and lower layers (a first pattern formed on a lower layer and a second pattern formed on an upper layer) or between different exposure patterns (a first pattern formed by the first exposure and a second pattern formed by the second exposure) in the DP on a wafer plane in a semiconductor device using a scanning charged particle microscope. As patterns are miniaturized, a demand for strict overlay accuracy is increasing, it is hard to ignore, for example, a mask manufacturing error, and deformation within a shot at the time of exposure (within an area exposed to light by single exposure light radiation. One to several chips are exposed by a single shot), and it is necessary to perform an overlay evaluation in a plurality of points in an exposure shot as well as a misalignment of all masks of each exposure shot.

In the method using the overlay evaluation-dedicated pattern formed on a wafer in advance which is disclosed in PTL 1, it is necessary to distributedly arrange dedicated patterns of a plurality of points within a shot, and thus there are cases in which it is hard to arrange, depending on a pattern layout. Further, in the method disclosed in PTL 2, since an overlay evaluation is performed using a normal circuit pattern other than a dedicated pattern, it is possible to estimate a close deviation amount, but since a dedicated pattern is not used, it is difficult to stably measure a deviation amount with a high degree of accuracy at any position, and there is a problem in a method of deciding and measuring an evaluation point.

Solution to Problem

In order to solve the above problems, according to the present invention, provided are a circuit pattern evaluation system and a method having the following features. As a result, it is possible to evaluate a close overlay deviation on a wafer plane with a high degree of accuracy. Through the following process, it is possible to automatically decide an evaluation point ("EP") or a measurement point in an EP based on layout information through a computer. Through the following process, it is possible for a user to decide an evaluation point ("EP") or a measurement point in an EP manually other than automatically.

(1) Provided is a pattern evaluation method of evaluating an overlay position between a first pattern formed on a sample by a first manufacturing process and a second pattern formed on the sample by a second manufacturing process using an image obtained by imaging an evaluation point on the sample through a scanning charged particle microscope, and pattern evaluation method includes a step of estimating imaging deviation allowed to evaluate an overlay position on one or more evaluation point candidates based on pattern layout information, a step of deciding one or more evaluation points from among the evaluation point candidates based on the allowed imaging deviation, a step of deciding an imaging sequence for imaging the selected evaluation point, and a step of evaluating an overlay position between first and second patterns based on an image obtained by imaging the evaluation point according to the imaging sequence. Further, in the step of estimating the allowed imaging deviation, the allowed imaging deviation is estimated so that it does not fail to specify the first pattern and the second pattern included in the evaluation point even when an imaging deviation occurs.

Here, a difference between the first pattern and the second pattern may be a layer difference such as upper and lower layers or may be a difference of multiple exposure in DP. Further, the number of patterns used to evaluate an overlay position may be two or more. For example, when patterns of three layers (upper, middle, and lower layers) are shown in an imaged image, it is possible to evaluate a deviation among first to third patterns, and when triple exposure (triple patterning) is performed as multiple exposure, it is possible to evaluate a deviation among first to third patterns. Further, when it is difficult to observe all patterns by single imaging, an overlay evaluation can be performed by performing imaging twice or more at timings of different manufacturing processes. As the pattern layout information, for example, pattern design data described in a GDSII format or an image obtained by imaging a pattern using a scanning charged particle microscope or an optical microscope may be used.

This feature will be further described. In imaging using a scanning charged particle microscope, imaging deviation is likely to occur. For this reason, an area including a pattern in which it does not fail in evaluation even when the imaging deviation occurs needs to be set as an evaluation point (referred to as an "EP"), and to this end, imaging deviation (which is referred to as "allowable imaging deviation") allowed to succeed in evaluation of an overlay position and actually occurring imaging deviation (which is referred to as "estimation imaging deviation") need to be estimated in each EP candidate and considered at the time of EP decision. In other words, an EP satisfying a relation of allowable imaging deviation≥estimation imaging deviation is selected. At this time, deviation of an exposure position of a pattern to be evaluated, shape deformation of the pattern, or a pattern change may be considered together. In other words, an EP in which it does not fail in evaluation of an overlay position even on an assumed pattern change is decided. The pattern layout information is used for estimation of the allowable imaging deviation. It is because the allowable imaging deviation differs according to a shape or an arrangement of patterns included in an EP. The estimation condition of the allowable imaging deviation includes (A) a condition in which it does not fail to specify the first pattern and the second pattern on the same imaging deviation, (B) a condition in which measurement positions of the first pattern and the second pattern are included in a field of view on the same imaging deviation, and the like. Particularly, there are cases in which a first pattern and a second pattern in an image are similar to each other in DP, the condition (A) is important.

In estimation of the estimation imaging deviation, the imaging sequence in the scanning charged particle microscope needs to be considered. Here, the imaging sequence will be further described. In order to image an EP with a high resolution without position deviation, it is necessary to image an EP after performing addressing or an image quality adjustment instead of imaging an EP suddenly. In a general imaging sequence, first, a unique pattern called an addressing point (which is referred to as "AP") is imaged, and a stage error or the like is estimated, or an auto-focus point (which is referred to as "AF") is imaged, a focus of charged particle beams is adjusted, and then an EP is imaged. For this reason, the imaging deviation changes, for example, according to whether there is an appropriate AP. In deciding the imaging sequence, it is effective to utilize the pattern layout information since it is necessary to understand a pattern present around an EP.

From the above, it is effective to decide an EP and an imaging sequence in view of each other. In other words, for each EP candidate, it is necessary to set an imaging sequence so that the estimation imaging deviation is the allowable imaging deviation or less, whereas when it is hard to set an imaging sequence in which the estimation imaging deviation is small, it is necessary to select an EP in which the allowable imaging deviation is large. When it is possible to input the allowable imaging deviation or the estimation imaging deviation in advance, it is possible to give the deviation as a processing parameter and perform the processing similarly.

Further, in decision of an EP, an imaging condition of an EP may be decided together in addition of a position of an EP. The imaging condition includes a field of view (imaging range or imaging magnification) of an EP, a probe current, an acceleration voltage, and a scanning direction of charged particle beams. For example, when a lower layer pattern is included in an EP, there are cases in which a pattern is not vividly observed on an image when an acceleration voltage is low. In this regard, when a lower layer pattern is included, a high acceleration voltage is considered to be set. When only patterns extending in the X direction are present in an EP, an edge in the X direction can be sharply imaged when the Y direction is set as the scanning direction of charged particle beams to be radiated to a sample. For this reason, it is effective to set a scanning direction according to a pattern direction in an EP.

(2) In the step of deciding the evaluation point, as the evaluation criterion for the evaluation point selection, (A) deformation easiness of each portion of a pattern is evaluated based on the layout information, and an evaluation point is decided based on the deformation easiness of each portion. Further, (B) both right and left edges of a pattern when the overlay position in the x direction is evaluated or both upper and lower edges of a pattern when the overlay position in the y direction is evaluated are included within the evaluation point for each of the first pattern and the second pattern.

This feature will be further described. In the item (1), the method of deciding an EP in view of robustness of an overlay evaluation on imaging deviation has been described, but the present item (2) is a method of considering robustness of an overlay evaluation on pattern deformation. Even when a pattern suitable for measurement is determined to be included in an EP based on a pattern shape in design data, there are cases in which it is actually difficult to perform stable overlay evaluation due to pattern deformation. As kinds of assumed pattern deformation, there are an increase/decrease in a pattern width, a recess of a line end, rounding of a corner portion, a pattern shift (parallel shift), and the like. In this regard, in the item (A), based on deformation easiness of each portion of a pattern, an EP is decided to include a portion which is unlikely to be deformed and a portion in which it does not fail in measurement although the portion is deformed so that stable measurement can be performed.

The item (B) is a method of deciding an EP in view of robustness, particularly, on an increase/decrease in a pattern width among assumed pattern deformation. When an increase/decrease of a pattern width is assumed to occur symmetrically when viewed from the center of the pattern in the first pattern and the second pattern, a deviation amount in central portions of the first pattern and the second pattern is considered not to significantly depend on an increase/decrease of a pattern width. Since edges of both opposite sides (upper and lower edges or right and left edges) of a pattern are necessary in order to obtain a position of a central portion of a pattern, it is effective to set an EP to include edges of both sides.

In the above method, an EP is decided in view of measurement easiness, but an EP may be decided while considering a point of view of measuring a pattern critical to device characteristics together. For example, an area including a pattern in which pattern deviation is determined to be likely to occur based on, for example, a lithography simulation installed in an Electronic Design Automation (EDA) tool may be preferentially selected as an EP. Alternatively, when position deviation occurs between a contact hole and an interconnection pattern electrically connecting upper and lower layers of stacked layers or position deviation occurs between a gate interconnection and an active layer in a transistor, this directly affects a change in device characteristics, and thus this area may be preferentially selected as an EP.

(3) When the first pattern is the lower layer pattern and the second pattern is the upper layer pattern in connection with stacked layers on the wafer, in the step of deciding the evaluation point, invisibility of the lower layer pattern by the upper layer pattern is estimated based on the layout information, and the evaluation point is decided in view of the invisibility.

This feature will be further described. Even when a pattern suitable for measurement is present in a lower layer, there are cases in which the pattern is hidden by an upper layer, and it is difficult to use the pattern in the imaged image. For this reason, invisibility of a pattern is estimated based on layout information and considered at the time of EP selection. Further, a lower layer does not overlap an upper layer pattern in layout information such as design data, but an actual pattern thereof may overlap an upper layer pattern due to pattern transfer position deviation. For this reason, it is effective to evaluate invisibility easiness of a pattern in view of a distance between an upper layer pattern and a lower layer pattern and consider it at the time of EP selection.

(4) In the step of deciding the evaluation point, plurality of EPs may be decided in view of an in-plane distribution of evaluation points on the sample. Specifically, (A) a plurality of areas are set on a sample, and at least one evaluation point is decided within each of the areas. Alternatively, (B) a condition related to a distance between two arbitrary evaluation points is given, and a plurality of evaluation points are decided to satisfy the condition.

This feature will be further described. In order to evaluate an overlay position in a plane, it is necessary to arrange EPs at an appropriate density within an evaluation range. In this case, when an arrangement is imbalanced, an area in which EPs are arranged at a low density decreases evaluation accuracy, and an area in which EPs are arranged at a high density results in a redundant evaluation. For this reason, for example, EPs are considered to be arranged at equal intervals in a grid form, but a pattern suitable for an overlay position evaluation is not necessarily present in each of EPs which are arranged in this way.

In this regard, in the item (A), a plurality of areas having a certain range in which each EP can be arranged are set. Since an EP can be set at any point in each of the areas, an EP in which overlay evaluation is possible is selected in each of the areas, for example, from a point of view of the item (1). Here, when areas in which each EP can be arranged are arranged in a plane, for example, at regular intervals, an EP in which overlay evaluation is possible can be arranged without significant imbalance in a distribution.

The item (B) is another example of solving the same problem, and a condition related to a distance between two arbitrary EPs, for example, a condition in which a distance between EPs is between A um and B um is given, and an EP candidate satisfying the corresponding condition is selected as an EP in which overlay evaluation is possible, and thus the overlay evaluation accuracy and the distribution without imbalance can be achieved.

(5) In the step of deciding the evaluation point, the evaluation point is decided by designating at least one or more evaluation points in advance, and searching another evaluation point including a pattern similar to a pattern included in the evaluation point based on the designated evaluation point.

This feature will be further described. An EP can be selected from various points of view according to an intention of the user who is an evaluator. Further, the EP differs according to a kind of a semiconductor device, a process or the like. However, since the overlay evaluation is performed at a plurality of positions, a task of registering a large amount of EPs to a recipe is not easy for the user. In this regard, a mechanism in which the user can input a desired EP is provided, and an EP similar to the input EP is automatically extracted as an EP candidate based on layout information. Thus, the user can save time and efforts of selecting a large amount of remaining EPs by inputting several EPs, and it is possible to rapidly cope with an EP selection criterion which differs according to the user, a kind, or a process.

Further, the user can designate all of the plurality of EPs. In this case, it is evaluated whether an EP designated by the user is an EP suitable for the overlay evaluation from a point of view of the items (1) to (4) or the item (6) which will be described later based on the layout information. If necessary, a process such as slightly shifting an EP position designated by the user to a position determined to be appropriate for the overlay evaluation or slightly changing the size of an EP can be performed. In this case, since an accurate position or size is automatically optimized only by designating an approximate EP position by the user, time and efforts can be saved.

(6) In the step of deciding the evaluation point, a measurement point used to evaluate the overlay position in the evaluation point is decided based on the pattern layout information. Further, similarly, the step of deciding the evaluation point includes a process of deciding a processing method of evaluating an overlay position in the evaluation point based on the pattern layout information for each evaluation point, and alternatives of the processing method include at least a method of imaging the evaluation point, comparing an obtained image with design data, and evaluating an overlay position (the processing method A) and a method of imaging the evaluation point, recognizing a pattern from an obtained image by image processing, and evaluating an overlay position (the processing method B).

This feature will be further described. There are a plurality of patterns in a decided EP, but it is necessary to measure a distance between the first pattern and the second pattern for the overlay evaluation. According to circumstances, there are cases in which all patterns are used for measurement of the distance, but, for example, distance measurement may be performed excluding a position at which pattern deformation is likely to occur as described above in the item (2). For this reason, the measurement point is decided for each evaluation pattern based on the layout information.

Furthermore, the processing method of obtaining the distance may be decided for each evaluation pattern. The process using design data as described above (the processing method A) and the process of obtaining a measurement value directly from an image as the above item (the processing method B) have advantages and disadvantages according to a pattern included in an EP, it is effective to decide the processing method for each EP based on the layout information.

On the other hand, in the step of deciding an EP, the user can designates the processing method for obtaining the distance in advance, and based on the layout information, an area in which the measurement value can be obtained by the processing method can be selected as an EP. Particularly, in processing of the processing method B, design data need not be used, and thus there may be the user who desires to select only an area in which processing of the processing method B is possible as an EP. In this case, at the time of recipe generation, for example, an EP is decided using design data, but there is a merit that it is unnecessary to handle design data at the time of imaging/measurement using a scanning charged particle microscope.

(7) In the step of deciding the evaluation point, a manufacturing process used to form an edge for each pattern edge is obtained as attribute information, and an evaluation point is decided based on the attribute information so that an edge formed by the first manufacturing process and an edge formed by a second manufacturing process are included in a field of view.

This feature will be further described. For example, transfer deviation between a first pattern transferred to a lower layer and a second pattern transferred to an upper layer in an overlay between layers is considered to be evaluated. Here, a part of the second pattern is assumed to have been removed by the cutting process. Here, there are cases in which it is difficult to evaluate the deviation even when a distance between an edge of the first pattern present on the lower layer and an edge of the second pattern present on the upper layer is simply measured. There are cases in which an edge of the second pattern used for measurement is formed by the cutting process, and deviation obtained in this case is deviation between the first pattern and the pattern of the cutting process. As described above, when deviation between two desired layers is evaluated, instead of simply selecting edges of the patterns present on the two layers and measuring the distance, it is necessary to select an edge used for measurement while considering a manufacturing process of forming an edge together. To this end, manufacturing process information is given for each edge as attribute information, and a combination of measurement target edges is decided based on the attribute information. This is not limited to the evaluation of the overlay deviation between layers, and is effective even when evaluating deviation among a plurality of processes between patterns formed on the same layer by a plurality of processes such as DP and self-aligned double patterning (SADP). The additional consideration of the attribute information is effective when a computer automatically decides an EP or a measurement point in an EP based on layout information, but it is also very effective even when the user decides an EP or a measurement point in an EP manually other than automatically. It is because there are cases in which it is difficult to anticipate a formed edge and a manufacturing process of forming the edge based on layout information of a pattern to be finally formed. Further, even when it is possible to anticipate it, knowledge related to a process or specifying pattern position is necessary for anticipation. Thus, as the layout information and the attribute information are shown to the user through a GUI or the like, it helps the user decide an EP or a measurement point in an EP.

(8) In the step of deciding the evaluation point, when the overlay position in the x direction is evaluated, first and second evaluation points are decided so that at least one of right and left edges of the first pattern and one of right and left edges of the second pattern are included in the first evaluation point, and one of the right and left edges of the first pattern and one of the right and left edges of the second pattern are included in the second evaluation point, and the overlay deviation is evaluated using the first and second evaluation points. Here, a direction of a pattern included in the first evaluation point and a direction of a pattern edge included in the second evaluation point are reversed right and left in the first and second patterns.

Similarly, when the overlay position in the y direction is evaluated, first and second evaluation points are decided so that at least one of upper and lower edges of the first pattern and one of upper and lower edges of the second pattern are included in the first evaluation point, and one of the upper and lower edges of the first pattern and one of the upper and lower edges of the second pattern are included in the second evaluation point, and the overlay deviation is evaluated using the first and second evaluation points. Here, a direction of a pattern edge included in the first evaluation point and a direction of a pattern edge included in the second evaluation point are upside down in the first and second patterns.

This feature will be further described. When the overlay evaluation is performed using a normal circuit pattern other than an overlay evaluation-dedicated pattern, it depends on a pattern layout whether there is an EP including a pattern suitable for overlay evaluation, and there is not necessarily a desired EP. For this reason, when the in-plane distribution of the overlay deviation is evaluated using an actual pattern, (problem 1) how to extract many EPs without imbalance and (problem 2) how to be able to calculate information effective for estimation of the in-plane distribution of the overlay deviation even when the number of extracted EPs is small remain to be solved. The present item is a process effective for the problem 1. In the item (2), as an example of an EP selection evaluation criterion, there is "(B) when the overlay position in the x direction is evaluated, both right and left edges of a pattern are included in the respective evaluation points, and when the overlay in the y direction position is evaluated, both upper and lower edges of a pattern are included in the respective evaluation points," for each of the first pattern and the second pattern, but there are cases in which little EP including all of a group of edges necessary for measurement in a field of view depending on a pattern layout. On the other hand, a method of increasing a possibility that there will be an EP satisfying the criterion by lowering an imaging magnification of an EP and increasing a field of view of an EP so that many patterns are included in a field of view is considered. Here, since the imaging magnification and the measurement accuracy are in the trade-off relation, there is a limitation to increase a field of view. In this regard, instead of estimating a deviation amount based on a single EP, a method of estimating a deviation amount based on two EPs is considered. In other words, there are cases in which when a group of edges necessary for measurement of deviation which is not included in a field of view in a single EP are divided into a first EP and a second EP and then imaged, all of a group of edges can be included in a field of view. Here, it is discovered that in order to prevent a deviation measurement value from being affected by an increase/decrease in a pattern width or imaging deviation of two EPs, it is necessary to image a group of edges necessary for measurement in the first EP and the second EP by the above-described combination. As two EPs are imaged to measure a single deviation amount as described above, the throughput of measurement decreases, but alternatives of EPs satisfying a measurement criterion increase, and a close in-plane deviation distribution is likely to be estimated without imbalance.

(9) In the step of deciding the evaluation point, a plurality of evaluation points in which a direction in which an overlay position is evaluable is set for each evaluation point are decided, and in the step of evaluating the overlay position, an overlay deviation vector at desired coordinates is calculated based on overlay deviation in a direction in which the overlay position is evaluable which is measured in each of the plurality of evaluation points.

This feature will be further described. The present item is effective to "(problem 2) how to be able to calculate information effective for estimation of the in-plane distribution of the overlay deviation even when the number of extracted EPs is small" described above in item (7), and a two-dimensional deviation vector (in the x and y directions) at certain coordinates is estimated by performing an interpolation process on the measurement value based on a measurable direction in each EP and a measured deviation amount. Even when the EP distribution is sparse or imbalance, it is possible that the close in-plane deviation distribution without imbalance can be estimated to some extent. Here, since reliability of the measurement value obtained by the interpolation process is not necessarily high, estimation reliability is calculated for each estimated deviation vector. When a deviation evaluation result is fed back to a semiconductor manufacturing device or the like to correct the deviation, a degree of adding a deviation vector can be controlled according to the reliability. As a method of calculating the reliability, a difference between interpolation and extrapolation in an interpolation process, a distance between an EP and an interpolation point, or the like may be used.

(10) In the step of deciding the evaluation point, evaluation point candidates are displayed according to the attribute information of the evaluation point. The attribute information described here includes not only the attribute information related to the manufacturing process described in item (7) but also attribute information (A) to (G) which will be described later.

This feature will be further described. In EP decision, it is effective to show a plurality of EP candidates to the user and enable the user to select an EP candidate from among the EP candidates, instead of automatically selecting all EPs. As a method of giving the user determination information for EP selection, positions of EPs on a wafer may be plotted and displayed in order to understand an in-plane distribution of EPs.

Further, various kinds of information decided in (1) to (9) can be displayed as the attribute information of the EP candidate. Examples of the attribute information include (A) allowable imaging deviation/estimation imaging deviation, (B) an imaging sequence/imaging condition/assumed imaging period of time, (C) deformation easiness of pattern used as a reference of evaluation stability, (D) invisibility of a pattern or invisibility easiness by deformation of a pattern, (E) a processing method of an evaluating measurement point/overlay position, (F) a direction of an evaluable overlay position, and (G) a manufacturing process of forming each pattern edge included in an EP. The direction of the evaluable overlay position of the item (F) is information representing that only an overlay position in the X direction or the Y direction is evaluable, that overlay positions in both X and Y directions are evaluable, or that an overlay position in an A° direction is evaluable. For example, when only a pattern edge changing in the X direction is included in an EP candidate, it is not possible to evaluate the overlay position in the Y direction. This information can be obtained by analyzing the layout information of the EP candidate.

Advantageous Effects of Invention

In order to understand a close in-plane distribution of an overlay position in a semiconductor device, a circuit pattern other than a dedicated pattern needs to be used as well. However, it is not easy to determine an area which is imaged and used for an excellent evaluation, and it is not easy to perform a task of registering a large amount of evaluation points to an imaging recipe. According to the present invention, it is possible to automatically create a recipe (set an evaluation point, an imaging sequence, and a measurement point/processing method) satisfying measurement requirements at a high speed.

DESCRIPTION OF EMBODIMENTS

The present invention provides a method of effectively inspecting an overlay of circuit patterns formed on a wafer with a high degree of accuracy using a scanning charged particle microscope in a process of designing or manufacturing a semiconductor device. In other words, provided is a method of closely estimating an overlay deviation between patterns of upper and lower layers (a first pattern formed on a lower layer and a second pattern formed on an upper layer) or between different exposure patterns (a first pattern formed by the first exposure and a second pattern formed by the second exposure) in DP on a wafer plane. This evaluation result is fed back to a correction parameter, pattern design data, or the like in a semiconductor manufacturing device such as an exposure device, and thus an improvement in exposure pattern overlay position accuracy and an increase in a process margin are expected.

Hereinafter, exemplary embodiments of the present invention will be described using a scanning electron microscope (SEM) which is a sort of the scanning charged particle microscope as an example. Examples of the scanning electron microscope include a critical dimension scanning electron microscope (CD-SEM) and a defect review scanning electron microscope (DR-SEM). However, the present invention is not limited to these examples, and can be applied to a scanning charged particle microscope such as a scanning ion microscope (SIM) as well. Further, the present invention is not limited to semiconductor devices, and can be applied to inspection of a sample having patterns which need to be subjected to overlay evaluation. Further, the following description will proceed in connection with, particularly, an embodiment in which an overlay deviation between a first pattern and a second pattern in an XY direction is evaluated, but as a variation of an overlay evaluation, an evaluation for a rotation between patterns and an evaluation for a change (transfer magnification) in a size between patterns are also included.

1. Image Imaging Device 1.1 SEM Components

Figure 2:
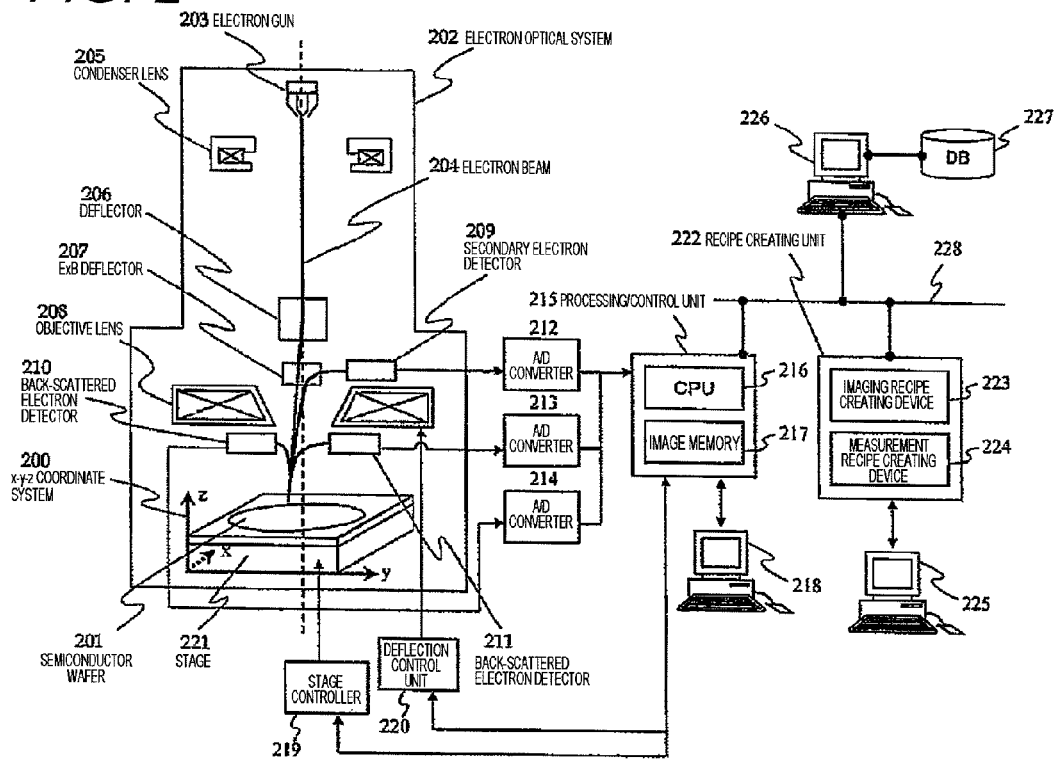
FIG. 2 is a diagram illustrating a configuration of an SEM device for implementing the present invention.

An exemplary evaluation system according to the present invention is illustrated in FIG. 2. FIG. 2 illustrates an embodiment using an SEM as an exemplary scanning charged particle microscope that images a sample to be evaluated, and is a block diagram illustrating components of an SEM that acquires a secondary electron image (SE image) or a back-scattered electron image (BSE image) of a sample. Further, an SE image and a BSE image are referred to as collectively an "SEM image." Further, an image acquired herein includes some or all of top-down images obtained by radiating electron beams to a measurement target in a vertical direction or tilt images obtained by radiating electron beams to a measurement target in an arbitrary oblique direction.

An electron optical system 202 includes an electron gun 203 therein, and generates electron beams 204. The electron beams emitted from the electron gun 203 are finely narrowed by a condenser lens 205, and then a radiation position of the electron beams and an aperture are controlled by a deflector 206 and an objective lens 208 so that the electron beams are radiated to be focused on a semiconductor wafer 201 serving as a sample placed on a stage 221. Secondary electrons and back-scattered electrons are emitted from the semiconductor wafer 201 to which the electron beams are radiated, and the secondary electrons separated from the trajectory of the radiated electron beams by an ExB deflector 207 are detected by a secondary electron detector 209. Meanwhile, the back-scattered electrons are detected by back-scattered electron detectors 210 and 211. The back-scattered electron detectors 210 and 211 are installed in different directions to each other. The secondary electrons and the back-scattered electrons detected by the secondary electron detector 209 and the back-scattered electron detectors 210 and 211 are converted into digital signals by analog to-digital (A/D) converters 212, 213, and 214, input to a processing/control unit 215, stored in an image memory 217, and subjected to image processing according to a purpose by a central processing unit (CPU) 216. FIG. 2 illustrates an embodiment in which two back-scattered electron image detectors are provided, but no back-scattered electron image detector may be provided, the number of back-scattered electron image detectors may be decreased or increased, or a detection direction may be changed.

Figure 3:
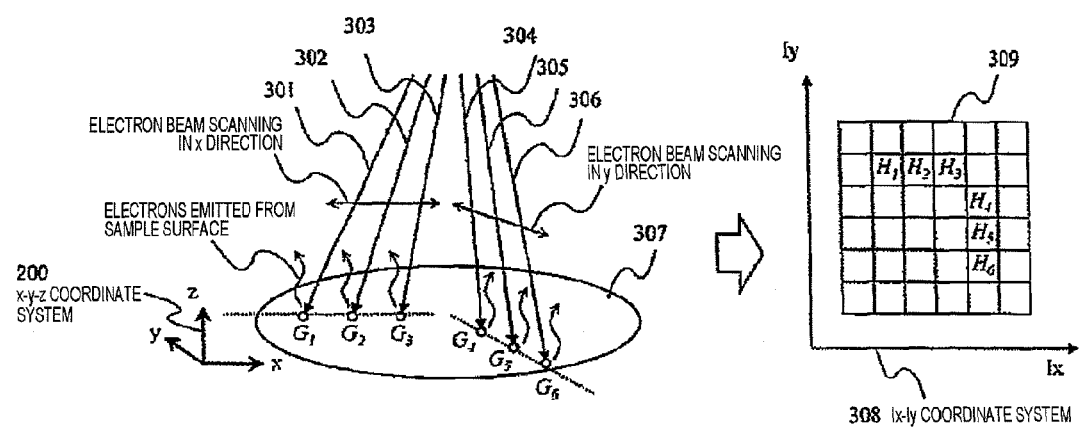
FIG. 3 is a diagram illustrating a method of imaging a signal amount of electrons emitted from a semiconductor wafer.

FIG. 3 illustrates a method of imaging a signal amount of electrons emitted from a semiconductor wafer when a semiconductor wafer 307 is scanned and irradiated with electron beams. As illustrated in the left of FIG. 3, electron beams 301 to 303 and 304 to 306 are scanned and radiated in x and y directions. It is possible to change a scanning direction by changing a deflection direction of electron beams. Positions on the semiconductor wafer irradiated with the electron beams 301 to 303 scanned in the x direction are denoted by G1 to G3. Similarly, positions on the semiconductor wafer irradiated with the electron beams 304 to 306 scanned in the y direction are denoted by G4 to G6. A signal amount of electrons emitted in the positions G1 to G6 are brightness values of pixels H1 to H6 (suffixes 1 to 6 in G and H correspond to each other) in an image 309 illustrated in the right of FIG. 3. A reference numeral 308 denotes a coordinate system (which is referred to as an "Ix-Iy coordinate system") representing the x and y directions on the image. As described above, the image frame 309 can be obtained by scanning an area in a field of view with the electron beams. Further, practically, a high S/N image can be obtained by scanning the area in a field of view with electron beams in the same manner and averaging obtained image frames. The number of frames to be added can be arbitrarily set.

In FIG. 2, the processing/control unit 215 is a computer system including the CPU 216 and the image memory 217, and transmits a control signal to a stage controller 219 or a deflection control unit 220 to image an area including a circuit pattern serving as an evaluation target based on an imaging recipe as evaluation pattern or performs various kinds of image processing or processing/control on an image obtained by imaging an arbitrary evaluation pattern on the semiconductor wafer 201.

The details of the imaging recipe will be described later. The measurement recipe is a file designating an image processing algorithm or a processing parameter used to measure a shape of a pattern or evaluate an overlay of a pattern or the like using an imaged SEM image, and an SEM processes an SEM image based on the measurement recipe to obtain an evaluation result. The imaging recipe and the measurement recipe are collectively referred to as simply a "recipe" when they are not distinguished from each other.

Further, the processing/control unit 215 is connected with a processing terminal 218 (which includes an input/output unit such as a display, keyboard, or a mouse), and includes a graphic user interface (GUI) for displaying an image or the like for the user or receiving an input from the user. A reference numeral 221 denotes an XY stage, and moves the semiconductor wafer 201 so that an image at an arbitrary position on the semiconductor wafer can be imaged. Changing an imaging position by the XY stage 221 is referred to as "stage shift," and changing an observation position, for example, by deflecting electron beams by the deflector 206 is referred to as "image shift." Generally, the stage shift is wide in a movable range but low in positioning accuracy of an imaging position, whereas the image shift is narrow in a movable range but high in positioning accuracy of an imaging position.

In FIG. 2, a recipe creating unit 222 is a computer system including an imaging recipe creating device 223 and a measurement recipe creating device 224. The recipe creating unit 222 is connected with a processing terminal 225, and includes a GUI for displaying a generated recipe for the user or receiving a setting related to imaging or recipe generation from the user.

The processing/control unit 215 can performs transmission and reception of information with the recipe creating unit 222 via a network 228. A database server 226 including a storage 227 is connected to the network, and may store and share some or all of (A) design data (mask design data (the absence/presence of optical proximity correction (OPC)) and design data of a wafer transfer pattern), (B) a simulation shape of an actual pattern estimated from the mask design data by a lithography simulation or the like, (C) generated imaging/measurement recipe, (D) imaged image (an optical microscope image and an SEM image), (E) imaging and evaluation results (a measurement value of a pattern shape of each portion of an evaluation pattern, a pattern contour, a deformation amount of a pattern, an overlay deviation amount or deviation direction between patterns, normality or abnormality of an overlay position, or the like), and (F) a decision rule of an imaging/measurement recipe in association with a kind, a manufacturing process, a date and time, a data acquiring device, or the like. Processes performed by the processing/control unit 215, the recipe creating unit 222, and the database server 226 may be divided and undertaken by a plurality of devices by an arbitrary combination or may be integrated and processed.

1.2 Imaging recipe

Figure 4:
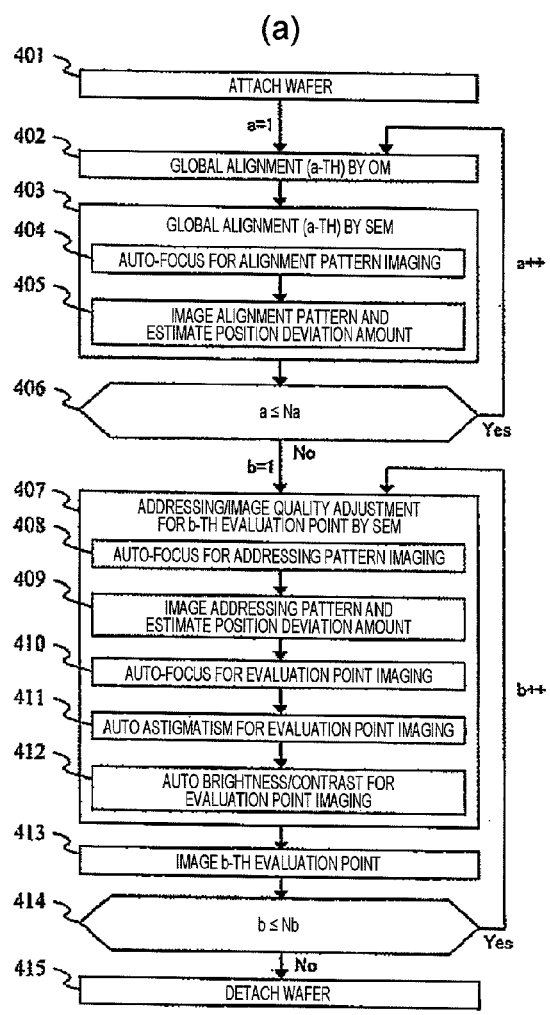
FIGS. 4(a) and 4(b) are diagrams illustrating an imaging sequence in an SEM device.
Figure 4:
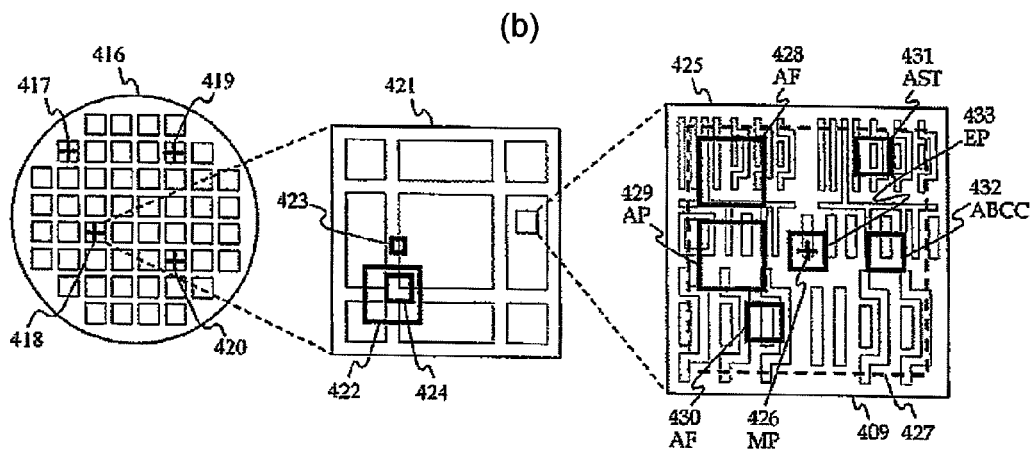

The imaging recipe is a file designating an imaging sequence of an SEM. In other words, the imaging recipe designates coordinates of an imaging area (which is referred to as an evaluation point (EP)) to be imaged as an evaluation target or an imaging sequence of imaging the EP with a high resolution without position deviation. There are a plurality of EPs on a wafer, and when the entire surface of a wafer is inspected, the wafer is filled with EPs. FIG. 4(a) is a flowchart illustrating a representative imaging sequence of imaging an EP, and FIG. 4(b) illustrates imaging positions corresponding to the representative imaging sequence. The imaging sequence will be described below with reference to FIGS. 4 (a) and 4(b).

First, in step 401 of FIG. 4(a), a semiconductor wafer (201 in FIGS. 2 and 416 in FIG. 4(b)) serving as a sample is attached to the stage 221 of the SEM device. In FIG. 4(b), square frames which are drawn in the wafer 416 and denoted by 417 to 420 represent chips, and a reference numeral 421 denotes an enlarged chip 418. Further, a reference numeral 425 denotes a portion of the chip 421 which is enlarged centering on an EP 433.

In step 402, through the stage shift, an image (which is referred to as an OM image) is obtained by moving a field of view of an optical microscope (not illustrated in FIG. 2) attached to an SEM to an alignment pattern on a previously designated wafer and imaging the alignment pattern on the wafer by the optical microscope. A deviation amount of a wafer is calculated by performing matching between previously prepared matching data (template) in the alignment pattern and the OM image. In FIG. 4(b), an imaging range of the alignment pattern is indicated by a thick frame 422.

In step 402, since an imaging magnification of the OM image is low, there are cases in which the accuracy of the deviation amount obtained by the matching is insufficient. Thus, in step 403, an SEM image is imaged by radiating the electron beams 204, and an alignment using the SEM image is performed. The field of view (which is referred to as "FOV") of the SEM is smaller than the FOV of the optical microscope, and thus a pattern to be imaged is likely to be outside the FOV depending on the deviation amount of the wafer, but since the deviation amount is made known by step 402, the radiation position of the electron beams 204 is moved in view of the deviation amount. Specifically, first, in step 404, the imaging position of the SEM is moved to an alignment pattern imaging auto-focus pattern 423, imaging is performed, an auto-focus adjustment parameter is obtained, and an auto-focus adjustment is performed based on the obtained parameter. Then, in step 405, the imaging position of the SEM is moved to an alignment pattern 424, imaging is performed, matching between previously prepared matching data (template) in the alignment pattern 424 and an SEM image is performed, a more accurate wafer deviation amount is calculated. FIG. 4(b) illustrates examples of imaging positions of the alignment pattern 422 for the optical microscope, the alignment pattern imaging auto-focus pattern 423 for the SEM, and the alignment pattern 424 for the SEM. The imaging positions needs to be selected while considering whether a pattern suitable for performing an alignment or an auto-focus is included.

The alignments using the optical microscope and the SEM in steps 402 and 403 are performed at a plurality of positions on the wafer, and a large original point deviation of the wafer or rotation of the wafer is calculated based on the position deviation amounts obtained at the plurality of positions (global alignment). FIG. 4(a) illustrates an example in which the alignment is performed at Na positions (step 406), and FIG. 4(b) illustrates an example in which the alignment is performed at four positions of the chips 417 to 420. Hereinafter, when the field of view is moved to desired coordinates, the moving is performed to cancel the obtained original point deviation and rotation.

After the wafer level alignment is completed, in step 407, high-accuracy positioning (addressing) and an image quality adjustment are performed on each evaluation pattern (EP), and the EP is imaged. The addressing is performed to cancel a stage shift error occurring when the field of view is moved to each EP. Specifically, the stage shift to the EP 433 is performed. In other words, the stage 221 is moved so that the vertical incident position of the electron beams 204 can be the center of the EP. The vertical incident position of the electron beams is called move coordinates (hereinafter, "MP"), and denoted by a cross mark 426. Here, the example of setting the MP as the central position of the EP is described, but the MP may be set around the EP. When the MP 426 is decided, a field of view movable range 427 (a dotted frame) is decided only by the image shift without moving the stage. Of course, even when the stage shift to the MP is performed, a deviation corresponding to a stop error of the stage shift occurs in practice. Then, in step 408, the imaging position of the SEM is moved to an addressing pattern imaging auto-focus pattern 428 (hereinafter, "AF") by the image shift, imaging is performed, an auto-focus adjustment parameter is obtained, and an auto-focus adjustment is performed based on the obtained parameter. Then, in step 409, the imaging position of the SEM is moved to an addressing pattern 429 (hereinafter, "AP"), imaging is performed, matching between previously prepared matching data (template) in the AP 424 and the SEM image is performed, and a stage shift error is calculated. Through the subsequent image shift, the field of view is moved to cancel the calculated stage shift error. Then, in step 410, the imaging position of the SEM is moved to the EP imaging AF 430 by the image shift, imaging is performed, an auto-focus adjustment parameter is obtained, and an auto-focus adjustment is performed based on the obtained parameter. Then, in step 411, the imaging position of the SEM is moved to an auto astigmatism pattern 431 (hereinafter, "AST") by the image shift, imaging is performed, an auto astigmatism adjustment parameter is obtained, and an auto astigmatism adjustment is performed based on the obtained parameter. The auto astigmatism represents astigmatism correction which is performed so that a cross-sectional shape of converged electron beams has a spot shape in order to acquire a non-deformed image at the time of SEM imaging. Then, in step 412, the imaging position of the SEM is moved to an auto brightness & contrast control pattern 432 (hereinafter, "ABCC") by the image shift, imaging is performed, an auto brightness & contrast control adjustment parameter is obtained, an auto brightness & contrast control adjustment is performed based on the obtained parameter. The auto brightness & contrast control represents performing a setting so that, for example, the highest portion and the lowest portion of an image signal have a full contrast or a contrast close thereto, for example, by adjusting a parameter such as a voltage value of a photomultiplier in the secondary electron detector 209 in order to acquire a vivid image having an appropriate brightness value and contrast at the time of EP imaging. The moving of the field of view to the AF for the AP, the AP for the EP, the AF, the AST, and the ABCC is performed by the image shift, and thus these patterns need to be set within the image shift allowable range 427.

After the addressing and the image quality adjustment are performed in step 407, in step 413, the imaging position is moved to the EP by the image shift, and imaging is performed.

After all EPs are imaged, in step 415, the wafer is detached from the SEM device.

In some cases, some of steps 404, 405, and 408 to 412 in which the alignment and the image quality adjustment are performed may be omitted, or an order thereof may be changed.

Further, due to the problem in which a contaminant is attached to a sample (contamination) by electron beam radiation, the adjustment points (AP, AF, AST, and ABCC) are generally set so that an EP does not overlap an imaging area. When the same area is imaged twice, due to influence of contamination, the second image becomes dark, a phenomenon in which a line width of a pattern changes remarkably appears. For this reason, in order to maintain the pattern shape accuracy of the EP used for evaluation of an evaluation pattern, various kinds adjustments are performed using a pattern around an EP, and thus radiation of electron beams to an EP is minimized by imaging an EP based on an adjusted parameter.

In this imaging sequence, coordinates of various kinds of imaging patterns (EP, AP, AF, AST, and ABCC), a size (a field of view or an imaging magnification), an imaging order (including a means for moving a field of view to each imaging pattern (the stage shift or the image shift)), an imaging condition (a probe current, an acceleration voltage, a scanning direction of electron beams, or the like), and the like are included. The imaging sequence is designated by the imaging recipe. Further, matching data (template) used for an alignment or addressing is also registered to the imaging recipe. Furthermore, a matching algorithm (an image processing method or an image processing parameter) in an alignment or addressing can be registered to the imaging recipe as well. The SEM images an EP based on the imaging recipe.

2. Method of Evaluating Pattern Overlay 2.1 Outline

According to the present invention, provided is a method of evaluating an overlay position between a first pattern formed on a sample by a first manufacturing process and a second pattern formed on the sample by a second manufacturing process using an image obtained by imaging the evaluation point on the sample by an SEM, and the method includes a step of estimating an imaging deviation allowed to evaluate an overlay position on one or more evaluation point candidates based on pattern layout information, a step of deciding one or more evaluation points from among the evaluation point candidates based on the allowed imaging deviation, a step of deciding an imaging sequence used to image the selected evaluation point, and a step of evaluating an overlay position between the first pattern and the second pattern from an image obtained by imaging the evaluation point according to the imaging sequence.

Further, in the step of estimating the allowed imaging deviation, the allowed imaging deviation is estimated so that it does not fail to specify the first pattern and the second pattern included in the evaluation point even when an imaging deviation occurs.

Here, a difference between the first pattern and the second pattern may be a layer difference such as upper and lower layers or may be a difference of multiple exposure in DP. Further, the number of patterns used to evaluate an overlay position may be two or more. For example, when patterns of three layers (upper, middle, and lower layers) are shown in an imaged image, it is possible to evaluate a deviation among first to third patterns, and when triple exposure (triple patterning) is performed as multiple exposure, it is possible to evaluate a deviation among first to third patterns. Further, when it is hard to observe all patterns by single imaging, an overlay evaluation can be performed by performing imaging twice or more at timings of different manufacturing processes. The following description will proceed with an example in which an overlay between two patterns (first pattern and second pattern) is evaluated.

Figure 1:
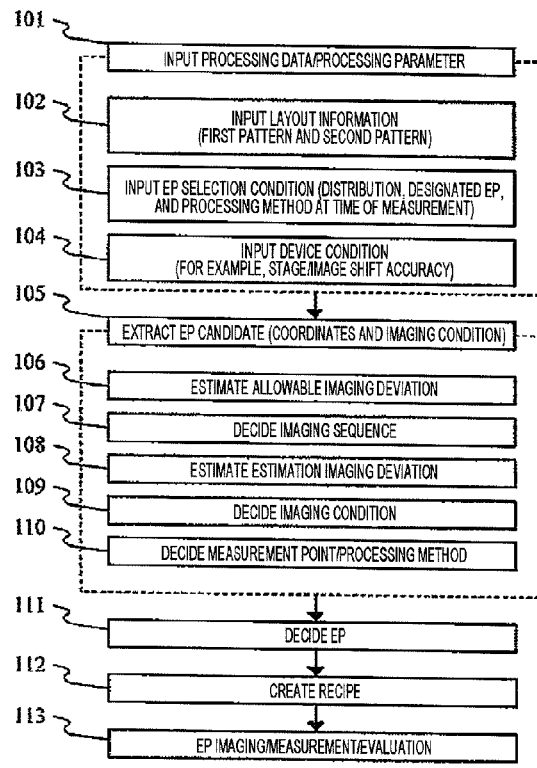
FIG. 1 is a diagram illustrating a processing sequence according to the present invention.

FIG. 1 illustrates an overall processing flow according to the present invention. First, in step 101, processing data and a processing parameter are input. As the processing data, pattern layout information serving as decision information for EP candidate extraction is input (step 102). As the pattern layout information, for example, pattern design data described in a GDSII format or an image obtained by imaging a pattern using a scanning charged particle microscope or an optical microscope may be used. Further, as the design data, any one of (A) mask design data (the absence/ presence of optical proximity correction (OPC)), (B) design data of a wafer transfer pattern, and (C) a simulation shape of an actual pattern estimated from the mask design data by a lithography simulation or the like may be used. The following description will proceed with an example in which (B) design data of a wafer transfer pattern is mainly used as the layout information. Further, the layout information includes the first pattern and the second pattern, and the first pattern and the second pattern may be managed using a single data file or may be managed using different data files.

Further, as one of the processing parameters, an EP selection condition and a device condition may be input (steps 103 and 104). The details of this input will be described later. Then, in step 105, EP candidates which can be used for overlay evaluation are extracted. An arbitrary range in which close overlay evaluation is desired to be performed may be set as an EP candidate extraction range, and all EPs which can be used for the overlay evaluation may be extracted in the range. Examples of the arbitrary range include all chips in a plane, a plurality of chips of an arbitrary combination, a range of a part in a chip, and a range between chips. Particularly, in order to evaluate deformation in a shot at the time of exposure, one to several chips in a single shot in an area exposed by single exposure radiation is considered to be a range in which the overlay evaluation is desired to be performed. In this step, allowable imaging deviation estimation, imaging sequence decision, and estimation imaging deviation estimation are performed (steps 106 to 108).

Figure 5:
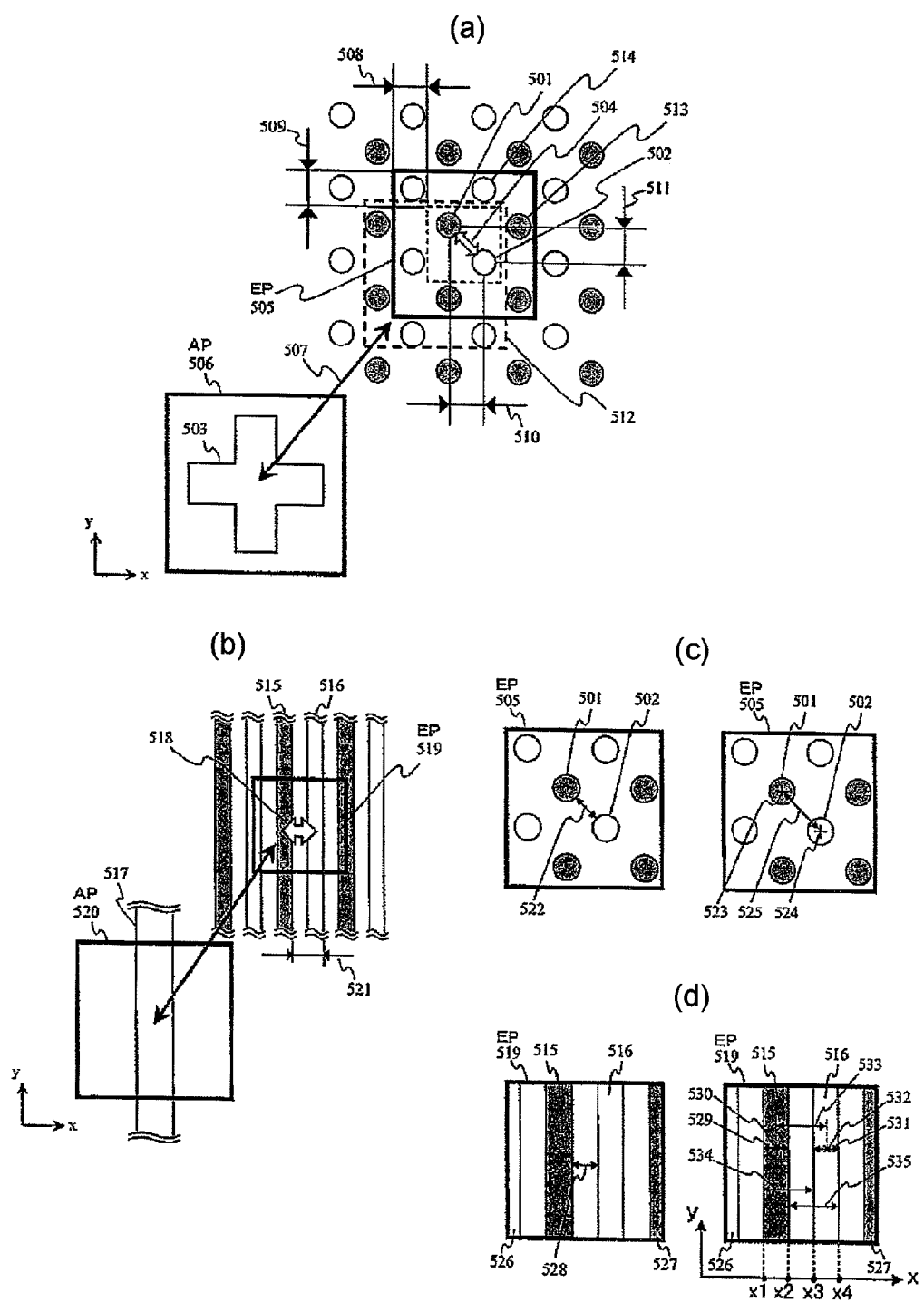
FIGS. 5(a) to 5(d) are diagrams illustrating a method of deciding an evaluation point and an imaging sequence in view of imaging deviation.

Steps 106 to 108 will be further described. FIG. 5(a) illustrates a selection example of an EP in which an overlay evaluation is performed. In FIG. 5(a), first patterns formed by the first exposure are indicated by patterns (for example, circular patterns 501 and 513) hatched by oblique lines, and second patterns formed by the second exposure are indicated by white patterns (for example, circular patterns 502 and 514 and a cross pattern 503). In other words, the circular patterns are arranged such that the first patterns and the second patterns are alternately lined up. Here, an EP 505 (a thick frame indicates an imaging range) is considered as an evaluation point to be imaged using an SEM in order to evaluate an overlay between the first pattern and the second pattern. It is possible to evaluate a positional relation 504 of the overlay, for example, based on the first pattern 501 and the second pattern 502 from an imaged image of the EP. In imaging using an SEM, imaging deviation is likely to occur. For this reason, an area including a pattern in which it does not fail in evaluation even when imaging deviation occurs needs to be set as an EP, and to this end, imaging deviation (which is referred to as "allowable imaging deviation") allowed to succeed in evaluation of an overlay position and actually occurring imaging deviation (which is referred to as "estimation imaging deviation") need to be estimated in each EP candidate and considered at the time of EP decision. In other words, an EP satisfying a relation of allowable imaging deviation estimation imaging deviation is selected. At this time, deviation of an exposure position of a pattern to be evaluated, shape deformation of the pattern, or a pattern change may be considered together. In other words, an EP in which it does not fail in evaluation of an overlay position even on an assumed pattern change is decided. The pattern layout information is used for estimation of the allowable imaging deviation. It is because the allowable imaging deviation differs according to a shape or an arrangement of patterns included in an EP. The estimation condition of the allowable imaging deviation includes (A) a condition in which it does not fail to specify the first pattern and the second pattern on the same imaging deviation, (B) a condition in which measurement portions of the first pattern and the second pattern are included in a field of view on the same imaging deviation, and the like. Particularly, there are cases in which a first pattern and a second pattern in an image are similar to each other in DP, the condition (A) is important.

In FIG. 5(a), the first pattern and the second pattern are displayed to look different as a hatched circle and a white circle, but in an actual SEM image, there are cases in which the first pattern and the second pattern are recognized as the same pattern and not distinguished from each other. For this reason, for example, when a pitch (510 in the x direction and 511 in the y direction) between the first pattern and the second pattern is indicated by P, and an EP imaging deviation of ±P/2 occurs, it is hard to specify the first pattern and the second pattern in the EP 505. Further, an expected maximum imaging deviation in the EP is assumed to 508 in the x direction and 509 in the y direction as illustrated in FIG. 5(a). In this case, an actual imaging position with respect to a set EP imaging position 505 may be a dotted frame 512 due to the imaging deviation. In the dotted frame 512, for example, the patterns 513 and 514 are outside the field of view. For this reason, when the imaging deviation is considered when the EP 505 is set, the fact that the patterns 513 and 514 are unlikely to be used for overlay evaluation has to be considered. As described above, it is necessary to decide an EP position and a field of view (imaging range or imaging magnification) in view of the imaging deviation.

In estimation of the estimation imaging deviation, the imaging sequence in the scanning charged particle microscope needs to be considered. Here, the imaging sequence will be further described. In order to image an EP with a high resolution without position deviation, it is necessary to image an EP after performing addressing or an image quality adjustment instead of imaging an EP suddenly. In a general imaging sequence, first, a unique pattern called an addressing point ("AP") is imaged, and a stage error or the like is estimated, or an auto-focus point ("AF") is imaged, a focus of charged particle beams is adjusted, and then an EP is imaged. For this reason, the imaging deviation changes, for example, according to whether there is an appropriate AP. In deciding the imaging sequence, it is effective to utilize the pattern layout information since it is necessary to understand a pattern present around an EP.

In FIG. 5(a), an AP 506 is set as the imaging sequence of the EP 505. The AP 506 includes the unique second pattern 503 in the field of view, and the stage shift error can be estimated when the AP 506 is moved by the stage shift. Further, when a distance 507 between the EP 505 and the AP 506 is within the image shift allowable range, movement of the field of view to the EP can be performed by the image shift, and field of view deviation of an EP can be suppressed within the image shift error. However, when a unique pattern such as the pattern 503 is not present nearby the EP 505, it is difficult to reduce the imaging deviation. On the other hand, when the allowable imaging deviation of the EP is larger than the stage shift error, it is unnecessary to perform addressing in the imaging sequence (the AP 506 is unnecessary).

From the above, it is effective to decide an EP and an imaging sequence in view of each other. In other words, for each EP candidate, it is necessary to set an imaging sequence so that the estimation imaging deviation is the allowable imaging deviation or less, whereas when it is hard to set an imaging sequence in which the estimation imaging deviation is small, it is necessary to select an EP in which the allowable imaging deviation is large. When it is possible to input the allowable imaging deviation or the estimation imaging deviation in advance, it is possible to give the same deviation as a processing parameter and perform processing similarly.

Further, in decision of an EP, an imaging condition of an EP may be decided together in addition of a position of an EP (step 109 in FIG. 1). The imaging condition includes a field of view (imaging range or imaging magnification) of an EP, a probe current, an acceleration voltage, and a scanning direction of charged particle beams. For example, when a lower layer pattern is included in an EP, there are cases in which a pattern is not vividly observed on an image when an acceleration voltage is low. In this regard, when a lower layer pattern is included, a high acceleration voltage is considered to be set. Further, when only patterns extending in the X direction are present in an EP, an edge in the X direction can be sharply imaged when the Y direction is set as the scanning direction of charged particle beams to be radiated to a sample. For this reason, it is effective to set a scanning direction according to a pattern direction in an EP.

Further, a measurement point in an EP or a processing method may be decided together (step 110 in FIG. 1). The measurement point is a portion of a pattern whose position is measured by image processing in order to quantitatively evaluate an overlay position in an EP, and the processing method is an image processing method of measuring a position. Referring to an EP 519 in FIG. 5(b), all pattern edges in the EP, right and left edges of patterns 515 and 516 in the EP, a right or left edge, or a right edge of the pattern 515 and a left edge of the pattern 516 may be used as the measurement point. Since there are cases in which a portion around an image is distorted, only edges near the center of an image may be used. Further, as the processing method, there is an image processing method or a method of utilizing design data. The details will be described later. The measurement point or the processing method may be decided for each EP.

FIG. 5(b) illustrates another selection example of an EP used to perform overlay evaluation. Similarly to FIG. 5(a), a first pattern is represented by a pattern (for example, 515) hatched by oblique line, and a second pattern is represented by a white pattern (for example, 516 or 517). In this example, since the first pattern and the second pattern are alternately arranged at pitches 521, 519 is considered to be imaged as an EP, and a positional relation 518 between patterns 515 and 516 is considered to be evaluated. Here, since in the EP 519, patterns extend long in the y direction, and there is no pattern edge changing in the x direction, only the overlay deviation in the x direction can be evaluated. However, when it is combined with a surrounding EP in which only the overlay deviation in the y direction can be evaluated, the overlay evaluation can be approximately performed in the x and y directions. Further, since the EP 519 and patterns therearound do not change in the y direction in terms of layout data, the overlay evaluation in the x direction can be performed in the EP even when the imaging deviation in the y direction slightly occurs. For this reason, an AP 520 is set as the imaging sequence of the EP 519. The AP 520 includes the unique second pattern 517 in the field of view in the x direction, and thus only the stage shift error in the x direction can be estimated, but as described above, it is not consequential when the allowable imaging deviation in the y direction is larger than the stage shift error in the EP 519. Of course, since measurement position accuracy is important in evaluating an overlay deviation distribution, even in this case, when a pattern in which addressing can be performed in the x and y directions is present nearby an EP, it is effective to set an AP including the pattern in the field of view.

Then, EPs are decided from among the EP candidates extracted in step 105 in FIG. 1 (step 111 in FIG. 1). Here, a group of EPs decided step 111 may be identical to a group of EP candidates extracted in step 105, or may be EPs which are selected or finely revised from a group of EP candidates shown to the user by the user. Then, the decided EPs are registered to a recipe (step 112 in FIG. 1). Here, the imaging sequence (decided in step 107), the imaging condition (decided in step 109), and the measurement point/processing method (step 110) for the EP may be registered to the recipe as well. Based on the created recipe, a plurality of EPs are sequentially imaged, measured, and subjected to overlay deviation evaluation (step 113). In the measurement, the positional relation between the first pattern and the second pattern is measured, and then, for example, a deviation amount from a design value can be evaluated.

An algorithm for implementing the above-described processing content or processing content which will be described later may be installed in a computer, and in this case, the computer can automatically perform some or all processes of steps 105 to 110 based on input processing data and processing parameters.

2.2 EP Candidate Extraction 2.2.1 EP Decision in View of Pattern Deformation

According to the present invention, in the step (step 105 or step 111 in FIG. 1) of deciding the evaluation point, deformation easiness of each portion of a pattern is evaluated based on layout information as an evaluation criterion for evaluation point selection, and an evaluation point is decided based on the deformation easiness of each portion.

This feature will be further described. The method of deciding an EP in view of robustness of overlay evaluation on imaging deviation has been described above, but robustness of overlay evaluation on pattern deformation can be additionally considered. Even when a pattern suitable for measurement is determined to be included in an EP based on a pattern shape in design data, there are cases in which it is actually difficult to perform stable overlay evaluation due to pattern deformation. As kinds of expected pattern deformation, there are an increase/decrease in a pattern width, a recess of a line end, rounding of a corner portion, a pattern shift (parallel shift), and the like. In this regard, based on deformation easiness of each portion of a pattern, an EP is decided to include a portion which is unlikely to be deformed and a portion in which it does not fail in measurement although deformed so that stable measurement can be performed.

Figure 6:
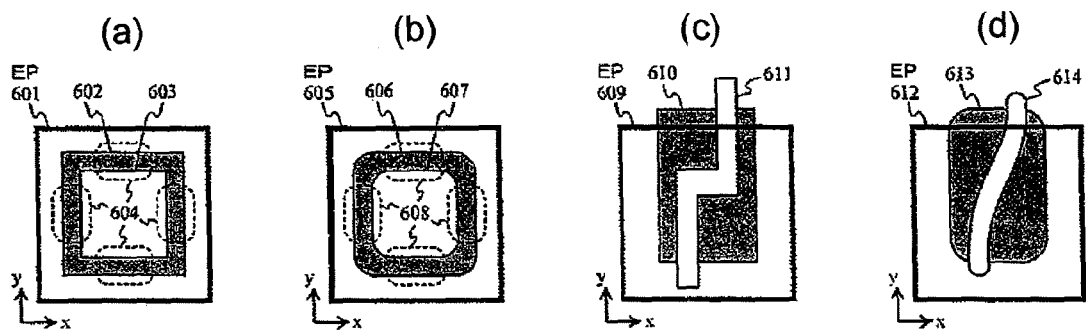
FIGS. 6(a) to 6(d) are diagrams illustrating a method of deciding an evaluation point in view of pattern deformation.

FIGS. 6(a) and 6(b) illustrate a difference in a shape between design data which is one of layout information and a pattern actually formed on a wafer. In FIG. 6(a), design data is rendered, and a lower layer pattern 602 and an upper layer pattern 603 are included in an EP 601. FIG. 6(b) illustrates an image obtained by imaging an actual pattern corresponding to FIG. 6(a), and an actual pattern 606 corresponding to the lower layer pattern 602 and an actual pattern 607 corresponding to the upper layer pattern 603 are included in an EP 605 obtained by imaging a portion corresponding to the EP 601. In the actual pattern, corner portions of the pattern are rounded, and it is difficult to measure the corner portions. Meanwhile, in areas which are at a short distance from the corner portions and indicated by dotted frames 604 and 608, pattern edges of a straight line form extend, and shape deformation is considered to be unlikely to occur although the corner portions are slightly rounded. For this reason, the overlay evaluation can be stably performed using an edge surrounded by the dotted frames 604 and 608. Shape deformation occurring as described above can be predicted from design data using a maximum rounding amount of the corner portion expected in the actual pattern as an input, and an area 601 can be extracted as an EP candidate together with decision of a measurement point (in this case, the dotted frame 604 servers as the measurement point). As a simulation shape of an actual pattern estimated from mask design data by a lithography simulation or the like is used as the layout information, an EP can be decided using a pattern close to actual pattern shapes 606 and 607. In this case, since a predicted error of a simulation occurs, it is effective to use an expected shape deformation amount together.

Similarly, FIGS. 6(c) and 6(d) illustrate another example showing a difference in a shape between design data and an actual pattern. In FIG. 6(c), design data is rendered, a lower layer pattern 610 and an upper layer pattern 611 are included in an EP 609. FIG. 6(d) illustrates an image obtained by imaging an actual pattern corresponding to FIG. 6(c), and an actual pattern 613 corresponding to the lower layer pattern 610 and an actual pattern 614 corresponding to the upper layer pattern 611 are included in an EP 612 obtained by imaging a portion corresponding to the EP 609. The upper layer pattern 614 is large in deformation in the actual pattern. A portion of an actual pattern corresponding to a portion bent in a crank form in design data gets blunt in shape due to an optical proximity effect or the like at the time of exposure. Further, in the actual pattern, an end portion of the pattern is rounded, and a position is recessed as well. For this reason, since there is no long straight line pattern suitable for measurement, it is not suitable for stable measurement. By predicting such deformation based on design data, an area 609 may not be extracted as an EP candidate or may be extracted as an EP candidate having a low evaluation value.

Further, according to the present invention, in the step (step 105 or step 111 in FIG. 1) of deciding the evaluation point, as the evaluation criterion for the evaluation point selection, right and left edges of a pattern when the overlay position in the x direction is evaluated or upper and lower edges of a pattern when the overlay position in the y direction is evaluated are included within the evaluation point for each of the first pattern and the second pattern.

This is a method of deciding an EP in view of robustness, particularly, on an increase/decrease in a pattern width among pattern deformation assumed in an actual pattern. When an increase/decrease of a pattern width is assumed to occur symmetrically when viewed from the center of the pattern in the first pattern and the second pattern, a deviation amount in central portions of the first pattern and the second pattern is considered not to significantly depend on an increase/decrease of a pattern width. Since edges of both opposite sides (upper and lower edges or right and left edges) of a pattern are necessary in order to obtain a position of a central portion of a pattern, it is effective to set an EP to include edges of both sides.

Figure 7:
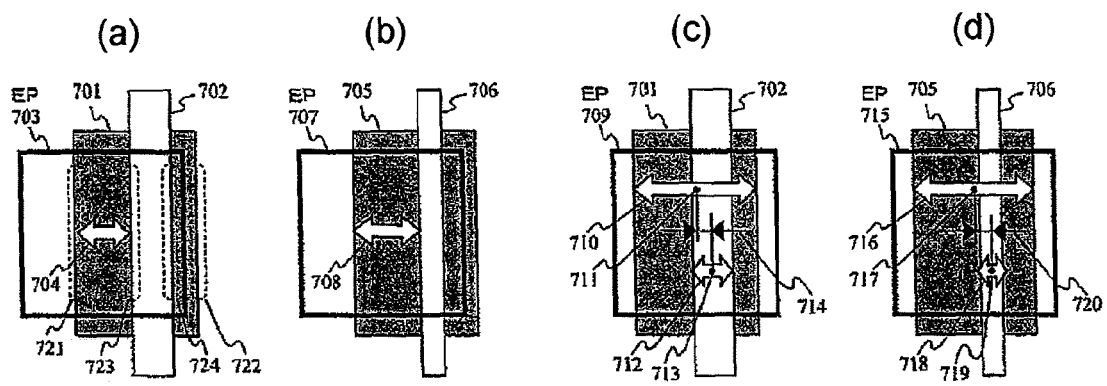
FIGS. 7(a) to 7(d) are diagrams illustrating a method of deciding an evaluation point in view of pattern deformation.

FIG. 7(a) illustrates an example in which an area 703 is set as an EP used to evaluate an overlay between a lower layer pattern 701 and the upper layer pattern 702 (the patterns 701 and 702 are pattern shapes on an imaged image). Here, a left end of the lower layer pattern 701 is referred to as a left edge (an edge surrounded by a dotted frame 721), and a right end thereof is referred to as a right edge (an edge surrounded by a dotted frame 722). Similarly, a left end of the upper layer pattern is referred to as a left edge (an edge surrounded by a dotted frame 723), and a right end thereof is referred to as a right edge (an edge surrounded by a dotted frame 724). In this example, by measuring a distance 704 between the left edge of the lower layer pattern and the left edge of the upper layer pattern, it is possible to evaluate an overlay between the upper and lower layers. However, this evaluation method is not robust to deformation of a pattern. FIG. 7(b) illustrates an example in which an area 707 is set as an EP used to evaluate an overlay between a lower layer pattern 705 and an upper layer pattern 706 (the patterns 705 and 706 are pattern shapes on an imaged image), but is the same in setting data of a pattern and a position of a set EP as FIG. 7(a). In this example, the upper layer pattern 706 is thinner than the upper layer pattern 702 due to a change in an exposure condition or the like. Here, a decrease in the width of the upper layer pattern symmetrically occurs when viewed from the center of the pattern, and a positional relation between the actual upper and lower layers does not change between FIGS. 7(a) and 7(b). However, as the upper layer pattern becomes thinner, the position of the left edge of the upper layer pattern shifts, and a distance 708 between the left edges of the upper and lower layer patterns is larger than the distance 704. Thus, the positional relation between the upper and lower layers is determined to have changed between FIGS. 7(a) and 7(b) in terms of the distance 708.

In order to solve this problem, an EP and a measurement point illustrated in FIG. 7(c) are considered. In FIGS. 7(a) and 7(c), the patterns of the upper and lower layers are identical, but an EP 709 of FIG. 7(c) is arranged to be deviated slightly to the right from the EP 703 of FIG. 7(a), and right and left edges of both the upper layer pattern and the lower layer pattern are included in the EP (the right edge surrounded by the dotted frame 722 of the lower layer pattern 701 is not included in the EP 703 of FIG. 7(a)). In this regard, the widths between the right and left edges in the upper and lower layers are measured (represented by widths 712 and 710), and middle points thereof are obtained (represented by black points 713 and 711). The positional relation between the upper and lower layers can be obtained by obtaining a distance 714 between the middle points. In other words, a deviation from a design value between the upper and lower layers can be obtained by subtracting a design value of the distance 714 from the measurement value of the distance 714. FIG. 7(d) illustrates the same pattern as that illustrated in FIG. 7(b), and the upper layer pattern becomes thinner. An EP is arranged at the same position 715 as the EP 709 of FIG. 7(c), and when pattern widths 718 and 716 of upper and lower layers, middle points 719 and 717 thereof, and a distance 720 between the middle points are obtained, the distance 720 between the middle points does not differ from the distance 714. In other words, as an EP and a measurement point are set as in FIGS. 7(c) and 7(d), the positional relation between the upper and lower layers can be obtained separately from an increase/decrease in a pattern width. FIGS. 7(a) to 7(d) illustrate an example in which the overlay in the x direction is evaluated, but when the overlay in the y direction is evaluated, an upper edge and a lower edge are desired to be included in an EP, and when the overlay in the x and y directions is evaluated, upper, lower, right, and left edges are desired to be included. Further, an effect of including opposite edges in an EP has been described in connection with an example of a processing method (which is a processing method belonging to (a processing method B) which will be described later) of detecting a pattern edge by image processing and evaluating overlay deviation, with reference to FIGS. 7(a) to 7(d), but the same effect can be expected even in a processing method (which is a processing method belonging to (a processing method A) which will be described later) of evaluating overlay deviation by a comparison of design data and an imaged image. For example, when design data differs from an imaged image in a corresponding pattern width, by performing an alignment between design data and an imaged image such that centers of opposite edges of both match, an error in the alignment by an increase/decrease in a pattern width can be reduced.

In FIGS. 6(a) to 7(d), the patterns of the upper and lower layers have been described as the first and second patterns as an example, but it is effective to consider pattern shape deformation similarly even in the first and second patterns formed by DP.

Here, when a concept of a measurement point that does not significantly depend on an increase/decrease in a pattern width is considered even on the measurement of FIGS. 5(a) and 5(b), the measurement illustrated in FIGS. 5(c) and 5(d) is considered. The drawings at the right and left of FIG. 5(c) illustrate two kinds of measurement methods when the overlay deviation between the first pattern and the second pattern is evaluated using the patterns 501 and 502 using the EP 505 selected in FIG. 5(a). In the left drawing of FIG. 5(c), the overlay deviation is evaluated by measuring a width 522 between pattern edges of the patterns 501 and 502, but as described above, the width 522 significantly changes even by an increase/decrease in a pattern width. On the other hand, in the right drawing of FIG. 5(c), the overlay deviation is evaluated by measuring a width 525 between a center 523 of the first pattern 501 and a center 524 of the second pattern 502. The width 525 rarely changes by an increase/decrease in a pattern width. Further, as a method of detecting a pattern center, a method of detecting a pattern edge by image processing and obtaining a pattern center from the edge is considered. Here, in the imaged image, there are cases in which the edge is not vivid, and it is difficult to detect the edge. In this case, a pattern center may be directly obtained by, for example, a center of gravity calculation of a brightness value nearby a pattern without detecting an edge.

The drawings at the right and left of FIG. 5(d) illustrate two kinds of measurement methods when the overlay deviation between the first pattern and the second pattern is evaluated using the patterns 515 and 516 using the EP 519 selected in FIG. 5(b). Similarly to the example of FIG. 5(c), in the left drawing of FIG. 5(d), the overlay deviation is evaluated by measuring a width 528 between pattern edges of the patterns 515 and 516, but in the right drawing of FIG. 5(d), the overlay deviation is evaluated by measuring a width 533 between a middle 530 of a width 529 of the first pattern 515 and a middle 532 of a width 531 of the second pattern 516. The width 533 rarely changes by an increase/decrease in a pattern width. When x coordinates of left and right edges of the pattern 515 are x1 and x2 and x coordinates of left and right edges of the pattern 516 are x3 and x4, the overlay deviation can be expressed by the following formula:

(Overlay deviation of second pattern on first pattern)= (middle point of width 531)−(middle point of width 529)=(x3+x4)/2−(x1+x2)/2=((x4−x2)−(x1−x3))/2=((width 535)−(width 534))/2

In other words, the overlay deviation may be measured by measuring the middle point of the width 531 and the middle point of the width 529 and obtaining a difference between the middle point of the width 531 and the middle point of the width 529 or by measuring the width 535 and the width 534 and obtaining a difference between the width 535 and the width 534. Here, it should be noted that the width 535 and the width 534 have a positive value or a negative value according to a positional relation between edges.

In the above method, an EP is decided in view of measurement easiness, but an EP may be decided while considering a point of view of measuring a pattern critical to device characteristics together. For example, an area including a pattern in which pattern deviation is determined to be likely to occur based on, for example, a lithography simulation installed in an Electronic Design Automation (EDA) tool may be preferentially selected as an EP. Alternatively, when position deviation occurs between a contact hole and an interconnection pattern electrically connecting upper and lower layers of stacked layers or position deviation occurs between a gate interconnection and an active layer in a transistor, this directly affects a change in device characteristics, and thus this area may be preferentially selected as an EP.

2.2.2 EP Decision in View of Invisibility of Lower Layer Pattern

According to the present invention, when the first pattern is the lower layer pattern and the second pattern is the upper layer pattern in connection with stacked layers on the wafer, in the step (step 105 or step 111 in FIG. 1) of deciding the evaluation point, invisibility of the lower layer pattern by the upper layer pattern is estimated based on the layout information, and the evaluation point is decided in view of the invisibility.

This feature will be further described. Even when a pattern suitable for measurement is present in a lower layer, there are cases in which the pattern is hidden by an upper layer, and it is difficult to use the pattern in the imaged image. For this reason, invisibility of a pattern is estimated based on layout information and considered at the time of EP selection.

Figure 8:
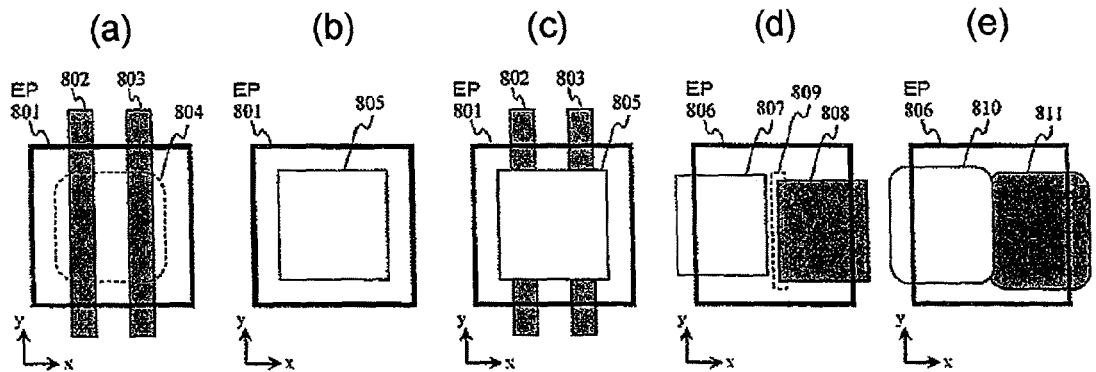
FIGS. 8(a) to 8(e) are diagrams illustrating a method of deciding an evaluation point in view of invisibility of a pattern.

FIGS. 8(a) to 8(c) illustrate patterns of respective layers or upper and lower layers which are drawn in an overlapping manner in the same position on the wafer, and for an EP 801, lower layer patterns 802 and 803 are illustrated in FIG. 8(a), an upper layer pattern 805 is illustrated in FIG. 8(b), and the patterns of the upper and lower layers are illustrated in an overlapping manner in FIG. 8(c). In setting data of the lower layer illustrated in FIG. 8(a), four pattern edges extending in a vertical direction are present within a dotted frame 804, but it is hard to use patterns in an actual imaged image since edges corresponding to the edges in the dotted frame 804 are not observed as illustrated in FIG. 8(c). As described above, it is necessary to decide an EP, a measurement point, an imaging sequence, or the like in view of invisibility of the lower layer pattern by the upper layer pattern.

Further, there is a case in which a lower layer does not overlap an upper layer pattern in layout information such as design data, but an actual pattern thereof may overlap an upper layer pattern due to pattern transfer position deviation. For this reason, it is effective to evaluate invisibility easiness of a pattern in view of a distance between an upper layer pattern and a lower layer pattern and consider it at the time of EP selection.

FIG. 8(d) illustrates design data in an EP 806 arranged at certain coordinates, and there are an upper layer pattern 807 and a lower layer pattern 808. Meanwhile, FIG. 8(e) illustrates actual patterns at the same position as in FIG. 8(d), and there are an actual pattern 810 corresponding to the upper layer pattern 807 in design data and an actual pattern 811 corresponding to the lower layer pattern 808 in design data. However, since the patterns of the upper and lower layers are expanded to be larger than in design data due to a change in the exposure condition or the like, a left edge (an edge surrounded by a dotted frame 809) of the lower layer pattern which can be observed in design data is hidden by the upper layer pattern and hardly observed in FIG. 7(e). This occurs even when a pattern shifts or is deformed as well as when a pattern is expanded. For this reason, when the EP 806 is selected under the assumption that the edge surrounded by the dotted frame 809 is used for measurement, the overlay evaluation using the same EP is likely to fail. By determining whether a pattern can be observed in view of pattern deformation as well as whether a pattern can be observed in design data as described above, an EP can be decided with a high degree of accuracy. Further, since it depends on a pattern deformation degree whether a pattern can be observed and a pattern deformation degree changes, there are cases in which it is difficult to uniformly determine whether a pattern can be observed based on only design data. For this reason, invisibility easiness of a pattern may be calculated based on a distance between patterns as attribute information of an EP and used for prioritization of EP selection. The invisibility easiness may be calculated based on an expected maximum pattern deformation amount which is input.

2.2.3 EP Decision in View of in-Plane Distribution of EP

According to the present invention, in the step (step 105 or step 111 in FIG. 1) of deciding the evaluation point, a plurality of EPs may be decided in view of an in-plane distribution of evaluation points on the sample. Specifically, (A) a plurality of areas are set on a sample, and at least one evaluation point is decided within each of the areas. Alternatively, (B) a condition related to a distance between two arbitrary evaluation points is given, and a plurality of evaluation points are decided to satisfy the condition.

This feature will be further described. In order to evaluate an overlay position in a plane, it is necessary to arrange EPs at an appropriate density within an evaluation range. In this case, when an arrangement is imbalanced, an area in which EPs are arranged at a low density decreases in evaluation accuracy, and an area in which EPs are arranged at a high density results in a redundant evaluation. For this reason, for example, EPs are considered to be arranged at equal intervals in a grid form, but a pattern suitable for an overlay position evaluation is not necessarily present in each of EPs which are arranged in this way. According to the conditions (A) and (B), it is possible to arrange an EP in which an overlay evaluation can be performed without significant imbalance in a distribution.

Figure 9:
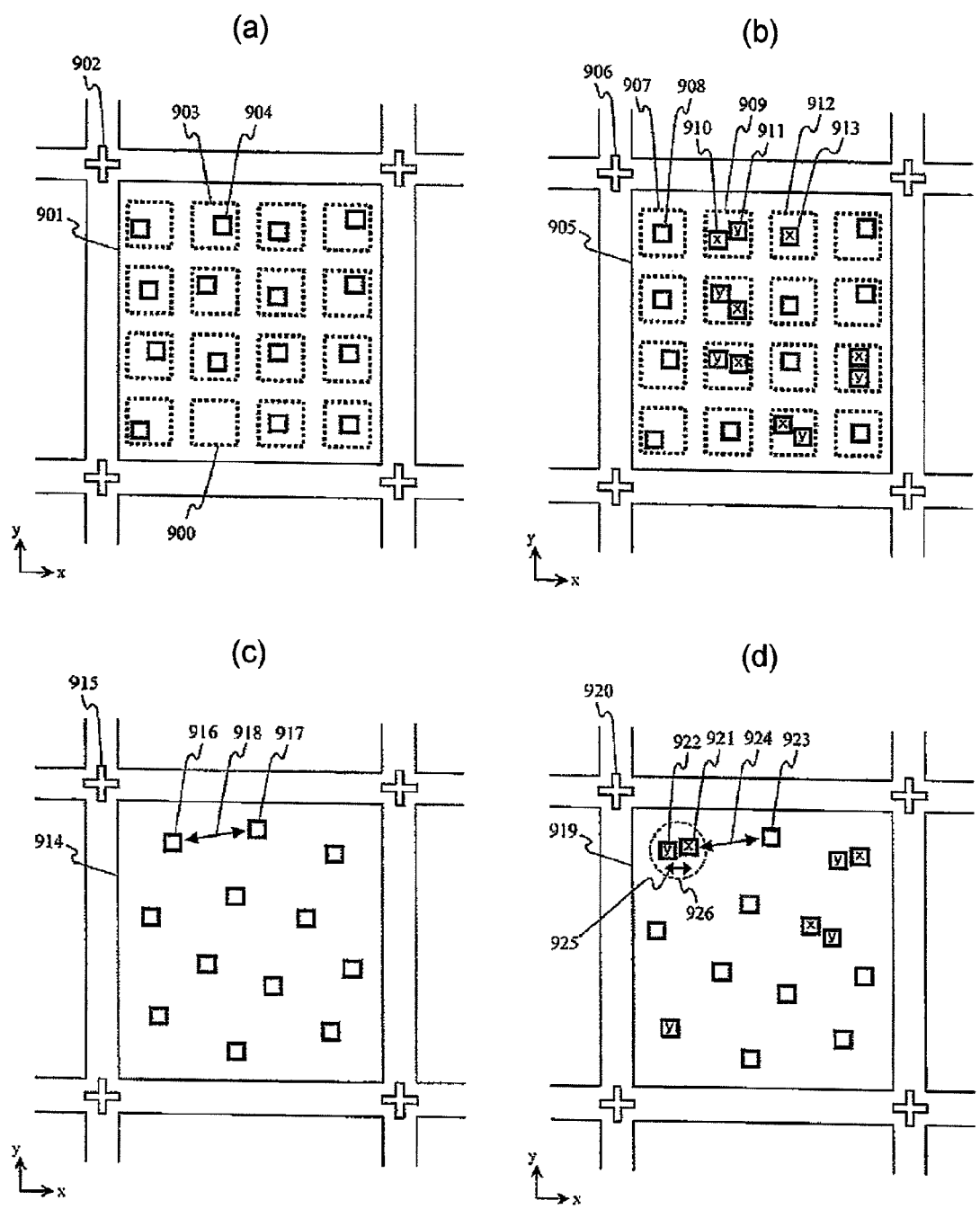
FIGS. 9(a) to 9(d) are diagrams illustrating a method of deciding an evaluation point in view of an in-plane distribution.

FIG. 9(a) is an enlarged view of a part of a wafer plane shape. Chips are arranged in a grid form, and a chip 901 is arranged at the center. In FIG. 9(a), four patterns dedicated to overlay evaluation are arranged in scribe areas near four corners of the chip (for example, cross marks 902). A chip and an arrangement of dedicated patterns are common in FIGS. 9(a) to 9(d) (chips 901, 905, 914, and 919 and dedicated patterns 902, 906, 915, and 920). In the overlay evaluation of the related art using only the dedicated pattern (for example, 902), deviation amount estimation positions are sparse, and it is difficult to understand an accurate in-plane tendency. In this regard, in this example, overlay evaluation is closely performed even in a chip. To this end, as an embodiment, a plurality of areas having a certain range in which each EP can be arranged are set. In FIG. 9(a), the area having a certain range is indicated by a dotted frame (for example, 903), and 16 (=4×4) areas are set in a grid form. Since an EP can be set at any point in the area, an EP in which overlay evaluation is possible is selected in each area from a point of view of the EP candidate extraction method. In the figure, a selected EP is indicated by a thick frame, and for example, an EP 904 is selected in an area 903. Here, when areas in which each EP can be arranged are arranged in a plane, for example, at regular intervals, an EP in which overlay evaluation is possible can be arranged without significant imbalance in a distribution. Further, in FIG. 9(a), a single EP is extracted in the area, but a plurality of EPs may be extracted from a single area. Further, there are cases in which an appropriate EP is not present in an area such as area 900, and thus it is hard to extract a candidate.

In FIG. 9(a), the number of areas in which an EP can be arranged is 16 (=4×4), but the number of areas, the width of an area, and the width between areas can be arbitrarily set. For example, when closer overlay evaluation is desired to be performed, the width of the area may be reduced to increase the number of areas. Further, an arrangement of the areas is not limited to a grid form, and an arrangement can be performed with another arbitrary degree of freedom. Further, in this example, a range in which the areas are arranged is the inside of the chip 901, but an arbitrary range in which close overlay evaluation is desired to be performed may be set, and the areas may be arranged within the range. Examples of the arbitrary range include all chips in a plane, a plurality of chips of an arbitrary combination, a range of a part in a chip, and a range between chips. Particularly, in order to evaluate deformation in a shot at the time of exposure, one to several chips in a single shot in an area exposed by single exposure radiation is considered to be a range in which the overlay evaluation is desired to be performed.

Further, as a variation of an EP to be decided, one in which overlay deviation between the first pattern and the second pattern can be evaluated in the x and y direction, one in which overlay deviation between the first pattern and the second pattern can be evaluated only in the x direction, and one in which overlay deviation between the first pattern and the second pattern can be evaluated only in the y direction can be combined. FIG. 9(b) illustrates, similarly to FIG. 9(a), an example in which 16 (=4×4) areas (for example, dotted frames 907, 909, and 912) in which an EP can be arranged are arranged in a grid form, and an EP is decided from each area. An EP decided in each area is indicated by a thick frame, but an EP (for example, 908) indicated by a white square is an EP in which overlay deviation can be evaluated in the x and y directions (referred to as "EPXY"). An EP (for example, 910 and 913) in which "x" is written in a square is an EP in which overlay deviation can be evaluated in the x direction (referred to as "EPX"; A pattern such as the EP 519 in FIG. 5(b)). An EP (for example, 911) in which "y" is written in a square is an EP in which overlay deviation can be evaluated in the y direction (referred to as "EPY"). It is desirable that the EPXY be present in all areas in which an EP can be arranged, but such good pattern is not necessarily present. In this regard, the EPX and the EPY may be added as an alternative of an EP. Particularly, an EPX 910 and an EPY 911 which are present therearound are selected as in the area 909, deviation amounts estimated from both EPs are merged, and thus the overlay deviation can be approximately evaluated in the x and y directions. Further, even when only an EPX 913 is selected as in the area 912, it helps the overlay evaluation. Here, as a variation of an EP, an EPXY, an EPX, and an EPY are described, but an EP in which an overlay position can be evaluated in an oblique direction, an EP in which rotation of a pattern can be evaluated, an EP in which a change (transfer magnification) in a size of a pattern can be evaluated, or the like may be used as a variation.

FIG. 9(c) illustrates another example of the method of deciding an EP in view of an in-plane distribution of EPs, and a condition related to a distance between two arbitrary EPs, for example, a condition in which a distance between EPs is between A um and B um is given, and an EP candidate satisfying the corresponding condition is selected as an EP in which overlay evaluation is possible, and thus the overlay evaluation accuracy and the uniform distribution can be achieved. In FIG. 9(c), a thick frame indicates an EP, and for example, 918 is given as a distance between an EP 916 and an EP 917. An arbitrary range in which close overlay evaluation is desired to be performed is set (a chip 914 in FIG. 9(c)), and an EP is decided so that a distance between arbitrary EPs satisfies the above condition.

FIG. 9(d) illustrates an example in which variations of an EPXY, an EPX, and an EPY are considered on FIG. 9(c) (notations of an EPXY, an EPX, and an EPY are the same as in FIG. 9(b)). As described above with reference to FIG. 9(b), there are cases in which there is no EPXY in an area in which an EP is desired to be arranged. In FIG. 9(d), when a distance with a neighboring EP is considered (for example, a distance 924 with an EP 923), a single EP is desired to set in a dotted frame 926, but there is assumed to be no EPXY in the dotted frame. In this case, when there is an EPX or an EPY, the EPX or the EPY may be selected as an EP, and when there are both an EPX and an EPY, both the EPX and the EPY may be selected. FIG. 9(d) illustrates an example in which both an EPX 921 and an EPY 922 are selected. At this time, when there are an EPX and an EPY therearound, the overlay deviation can be approximately evaluated in the x and y directions, and thus the EPX and the EPY may be arranged to be close to each other. For this reason, as a condition related to a distance between EPs, a condition related to a distance (for example, 925) between an EPX and an EPY and a condition related to a distance (for example, 924) between normal EPs can be separately given (in this example, the distance 925<the distance 924).

2.2.4 EP Decision Based on User Designation of EP

According to the present invention, in the step (step 105 or step 111 in FIG. 1) of deciding the evaluation point, the evaluation point is decided such that at least one or more evaluation points are designated in advance, and another evaluation point including a pattern similar to a pattern included in the evaluation point is searched based on the designated evaluation points.

This feature will be further described. An EP can be selected from various points of view according to an intention of the user who is an evaluator. Further, an EP differs according to a kind of a semiconductor device, a process or the like. However, when the overlay evaluation is performed at a plurality of positions, a task of registering a large amount of EPs to a recipe is not easy to the user. In this regard, a mechanism in which the user can input a desired input is provided, and an EP similar to the input EP is automatically extracted as an EP candidate based on layout information. Thus, the user can save time and efforts of selecting a large amount of remaining EPs by inputting several EPs, and it is possible to rapidly cope with an EP selection criterion which differs according to the user, a kind, or a process.

Figure 10:
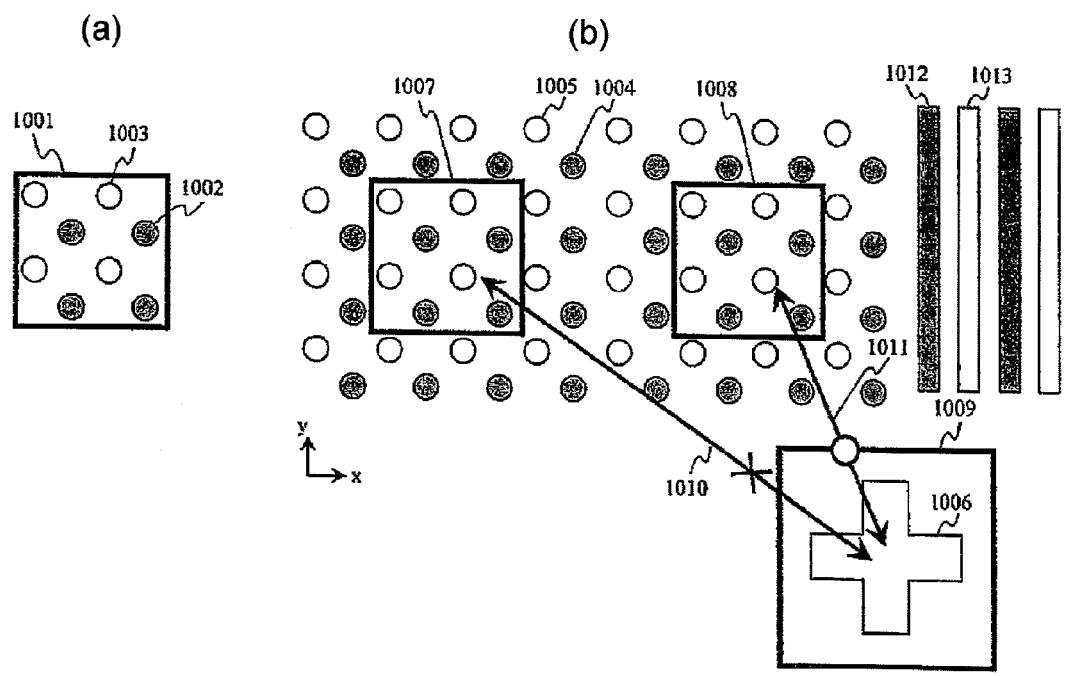
FIGS. 10(a) and 10(b) are diagrams illustrating a method of deciding an evaluation point based on user designation.

FIG. 10(a) illustrates an EP 1001 as an example of an EP designated by the user. In the EP, there are patterns (for example, 1002) hatched by oblique lines and white patterns (for example, 1003) as first patterns formed by the first exposure and second patterns formed by the second exposure. The designating may be performed on layout data and may be performed on an image. FIG. 10(b) illustrates a result of extracting an EP candidate similar to a designated EP from layout data using the EP 1001 as an input. In FIG. 10(b), similarly, first patterns are indicated by patterns (for example, 1004 and 1012) hatched by oblique lines, and second patterns are indicated by white patterns (for example, 1005, 1006, and 1013). A range in which a similar EP candidate is extracted can be arbitrarily set, and in FIG. 10(b), a part of the range is illustrated, but EPs 1007 and 1008 similar to the designated EP 1001 are extracted. In the present invention, not only a pattern similar to a designated EP can be simply extracted, but also a similar EP can be extracted in view of an imaging sequence as well. In other words, in the extracted similar EP 1008, a unique pattern 1006 is present within the image shift allowable range (a distance 1011 between the similar EP 1008 and the pattern 1006 is within the image shift allowable range), and the imaging deviation of the similar EP 1008 can be suppressed to be the allowable position deviation or less by setting an AP 1009 and performing addressing, but in the similar EP 1007, it is difficult to set such an AP (the distance 1011 between the similar EP 1007 and the pattern 1006 is outside the image shift allowable range). As the decision of the imaging sequence is performed together as described above, it is possible to exclude the similar EP 1007 from the extraction candidate, and it is possible to increase the EP extraction accuracy. In addition, in the example of FIG. 10(b), one similar EP, that is, the EP 1008 is finally extracted, but in the present invention, it is possible to extract all of the plurality of similar EPs present in an EP candidate extraction range and show the extracted EPs to the user.

Figure 11:
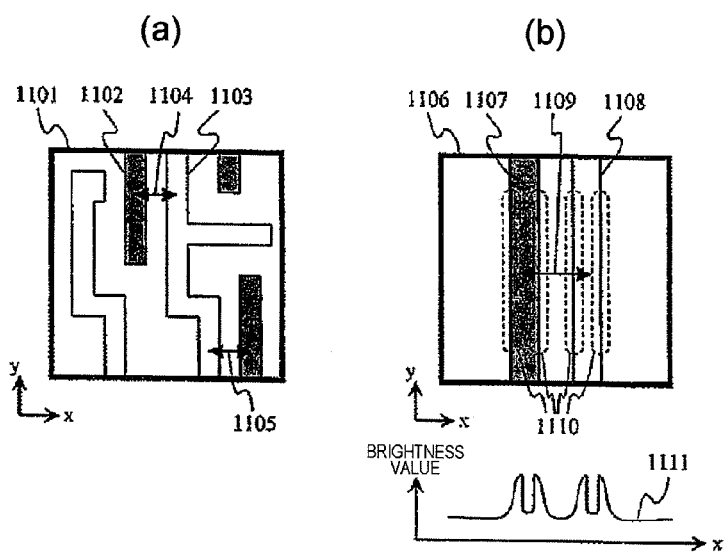
FIGS. 11 (a) and 11(b) diagram illustrating a variation of a measurement point/processing method.

Further, the user can designate all a plurality of EPs. In this case, it is evaluated whether an EP designated by the user is an EP suitable for the overlay evaluation from a point of view of the EP selection criterion described above with reference to FIGS. 5(a) to 9(d) or a point of view of the measurement point/processing method which will be described later with reference to FIGS. 11(a) and 11(b) based on the layout information. If necessary, a process such as slightly shifting a position of an EP designated by the user to a position determined to be appropriate by the overlay evaluation or slightly changing the size of an EP can be performed. In this case, since an accurate position or size is automatically optimized as the user designates an approximate EP position, time and efforts can be saved.

For example, when the EP 703 of FIG. 7(a) is given as the position of an EP designated by the user, the EP can be moved to the position of the EP 709 of FIG. 7(c) in which the higher overlay accuracy can be expected.

2.2.5 EP Decision in View of Attribute Information Related to Manufacturing Process According to the present invention, in the step (step 105 or step 111 in FIG. 1) of deciding the evaluation point, a manufacturing process used to form an edge for each pattern edge is obtained as attribute information, and an evaluation point is decided based on the attribute information so that an edge formed by the first manufacturing process and an edge formed by the second manufacturing process are included in a field of view.

Figure 19:
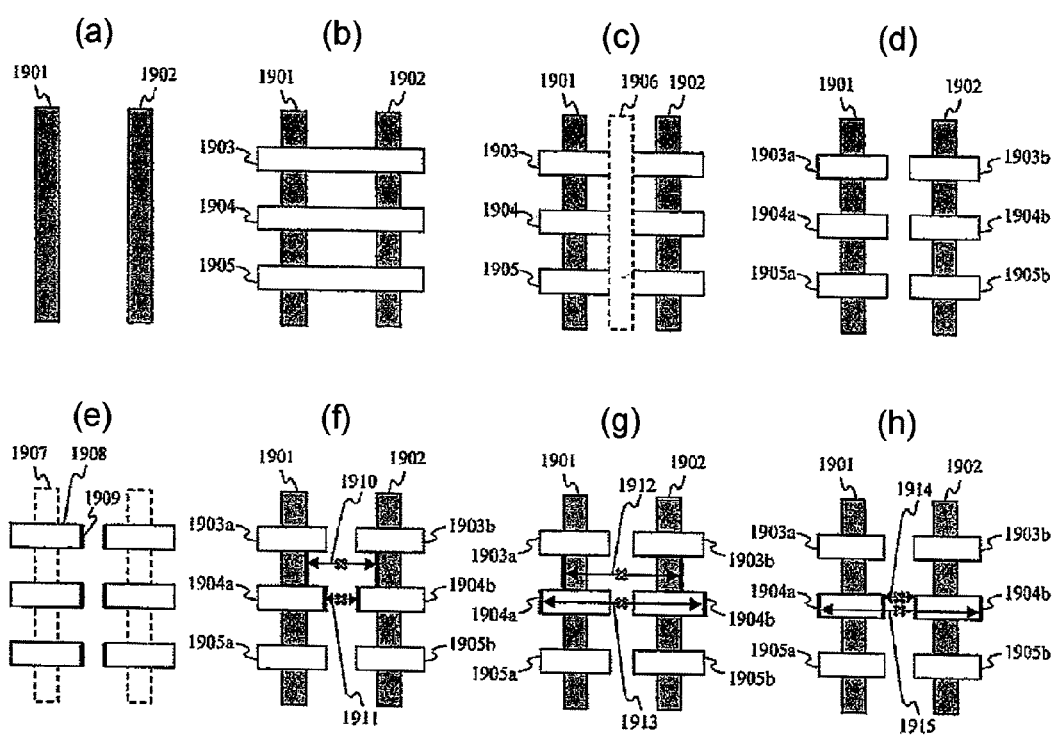
FIGS. 19(a) to 19(h) are diagrams illustrating a method of allocating attribute information related to a manufacturing process to each edge and deciding a measurement point based on the attribute information.

This feature will be further described. As an example, overlay deviation between upper and lower layer patterns illustrated in FIG. 19(d) is evaluated. In FIG. 19(d), patterns (1901 and 1902) hatched by oblique lines are illustrated as first patterns formed on a lower layer by the first exposure (a first manufacturing process), and white patterns (1903a to 1905a and 1903b to 1905b) are illustrated as second patterns formed on an upper layer by the second exposure (a second manufacturing process) (technically, as will be described later, the patterns 1903a to 1905a and 1903b to 1905b are formed by the second manufacturing process and a cutting process). A process of forming the patterns is illustrated in FIGS. 19(*a*) to 19(*c*). First, as illustrated in FIG. 19(*a*), the first patterns 1901 and 1902 are formed by the first exposure. Then, as illustrated in FIG. 19(*b*), the second patterns 1903 to 1905 are formed by the second exposure. Lastly, as illustrated in FIG. 19(*c*), the second pattern remaining in an area 1906 is removed by a process called a cutting process. In the cutting process, the second pattern in the area 1906 may be removed by causing the area 1906 to be exposed to light as an exposure pattern, or the second pattern in the area 1906 may be removed by radiating electron beams to the area 1906 by direct writing of electron beams.

When the overlay deviation between the first and second patterns is evaluated on such a pattern, there are cases in which it is difficult to evaluate the deviation even when a distance between an edge of the first pattern present on the lower layer and an edge of the second pattern present on the upper layer is simply measured. This example is illustrated in FIG. 19(*f*). In FIG. 19(*f*), the deviation between the upper and lower layer patterns is evaluated by subtracting a design value of a distance between middle points from a distance between a middle point (indicated by an x mark on an arrow indicating a width 1911) of the width 1911 between a right edge (indicated by a thick line) of an upper layer pattern 1904a and a left edge (indicated by a thick line) of an upper layer pattern 1904b and a middle point (indicated by an x mark on an arrow indicating a width 1910) of the width 1910 between a right edge (indicated by a thick line) of a lower layer pattern 1901 and a left edge (indicated by a thick line) of a lower layer pattern 1902 (the widths 1911 and 1910 correspond to the widths 712 and 710 in the measurement example of FIG. 7(*c*)). However, since the right edge of the upper layer pattern 1904a and the left edge of the upper layer pattern 1904b are edges formed by the cutting process, the deviation obtained from the widths 1911 and 1910 is overlay deviation between the first pattern and the pattern of the cutting process other than the overlay deviation between the first and second patterns. As described above, when overlay deviation between two desired layers is evaluated, instead of simply selecting edges of patterns present on the two layers and measuring a distance between the edges, it is necessary to select an edge used for measurement while considering a manufacturing process used to form an edge together. To this end, manufacturing process information is given for each edge as attribute information, and a combination of measurement target edges is decided based on the attribute information. FIG. 19(*e*) illustrates edges according to the attribute information. An edge indicated by a dotted line, that is, an edge 1907 is an edge formed by the first manufacturing process, an edge indicated by a fine solid line, that is, an edge 1908 is an edge formed by the second manufacturing process, and an edge indicated by a thick solid line, that is, an edge 1909 is an edge formed by the cutting process. As the attribute information related to the manufacturing process of the edge as well as the edge direction is considered, an edge to be recognized to obtain deviation between processes which are desired to be evaluated can be appropriately selected. As described above, the attribute information is given in units of edges (segments) other than units of closed figures of patterns. Based on the attribute information, it is possible to determine whether an edge used for measurement is an edge formed by a process which is desired to be evaluated.

According to the attribute information, in order to evaluate the overlay deviation between the first and second patterns, it is understood that it is desirable to perform the measurement illustrated in FIG. 19(*g*). In this example, the deviation between the first and second patterns can be evaluated based on a distance between a middle point of a width 1913 between the left edge of the upper layer pattern 1904a (having the attribute information generated by the second manufacturing process according to FIG. 19(*e*)) and the right edge of the upper layer pattern 1904b (having the attribute information generated by the second manufacturing process according to FIG. 19(*e*)) and a middle point of a width 1912 between the left edge of the lower layer pattern 1901 (having the attribute information generated by the first manufacturing process according to FIG. 19(*e*)) and the right edge of the lower layer pattern 1902 (having the attribute information generated by the second manufacturing process according to FIG. 19(*e*)).

Similarly, when deviation between the second pattern and the pattern of the cutting process is evaluated, it is understood from the attribute information that it is desirable to perform, for example, the measurement illustrated in FIG. 19(*h*). In this example, the second pattern and the pattern of the cutting process can be evaluated based on a distance between a middle point of a width 1915 between the left edge of the upper layer pattern 1904a (having the attribute information generated by the second manufacturing process according to FIG. 19(*e*)) and the right edge of the upper layer pattern 1904b (having the attribute information generated by the second manufacturing process according to FIG. 19(*e*)) and a middle point of a width 1914 between the right edge of the upper layer pattern 1904a (having the attribute information generated by the cutting process according to FIG. 19(*e*)) and the left edge of the upper layer pattern 1904b (having the attribute information generated by the cutting process according to FIG. 19(*e*)).

Further, when design data is used as the layout information, and it is difficult to obtain final pattern design data (intent design data) which is formed at the time of imaging and illustrated in FIG. 19(*d*), intent design data is generated based on design data of each of the processes illustrated in FIGS. 19(*a*) to 19(*c*) and layer information of each process or information representing whether it is the cutting process. Attribute information is obtained based on the intent design data, and an EP or a measurement point in an EP is decided based on the intent design data and the attribute information. If there is intent design data but it is difficult to obtain design data of each process, attribute information is allocated to the intent design data based on layer information of each process or information of the cutting process, and an EP or a measurement point in an EP is decided.

Figure 20:
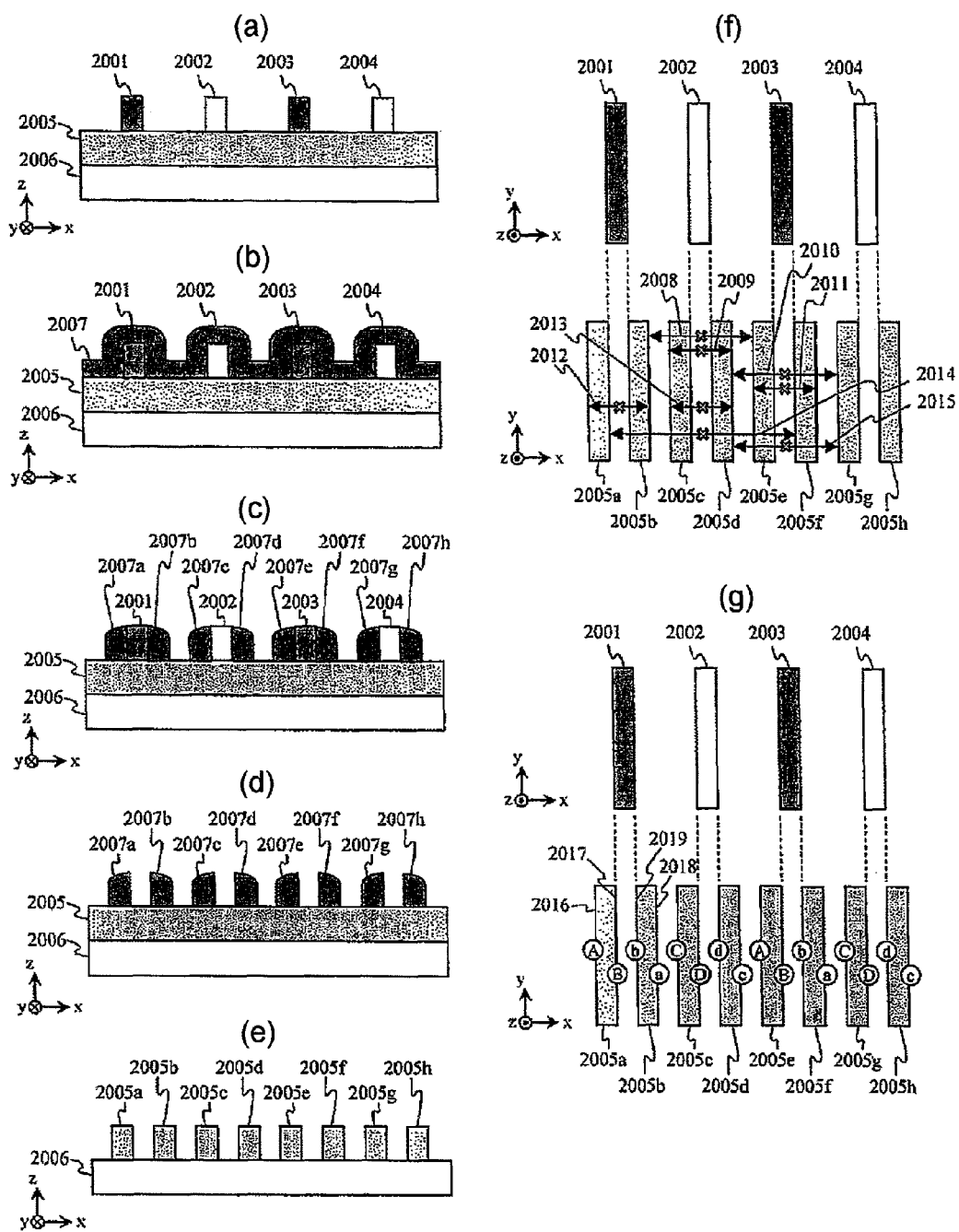
FIGS. 20(a) to 20(g) are diagrams illustrating a method of allocating attribute information related to a manufacturing process to each edge and deciding a measurement point based on the attribute information.

The deciding of an EP or a measurement point in an EP using the attribute information is not limited to the evaluation of the overlay deviation between layers described above with reference to FIGS. 19(*a*) to 19(*h*), but is effective even when deviation among the plurality of processes between patterns formed on the layer by a plurality of processes such as DP and self-aligned double patterning (SADP). Here, deciding an EP or a measurement point in an EP using attribute information in SADP will be described with reference to FIGS. 20(*a*) to 20(*g*) as an example. First, an example of a manufacturing process of SADP will be briefly described with reference to cross-sectional views of a wafer illustrated in FIGS. 20(*a*) to 20(*e*). First, patterns 2001 to 2004 are formed on the top surface of a base layer 2006 and a hard mask layer 2005 by DP as described in the background art as illustrated in FIG. 20(*a*). In other words, the first patterns 2001 and 2003 indicated by patterns hatched by oblique lines are formed, and then second patterns 2002 and 2004 indicated by white patterns are formed in a space between the first patterns. Then, a resist film 2007 is deposited on the wafer surface as illustrated in FIG. 20(b), and then patterns 2007a to 2007h called sidewall spacers are formed on sidewalls of the patterns 2001 to 2004 by etching as illustrated in FIG. 20(c). Then, the patterns 2001 to 2004 are removed as illustrated in FIG. 20(d), and then the hard mask layer 2005 is etched using the sidewall spacers 2007a to 2007h as a mask to form patterns 2005a to 2005h as illustrated in FIG. 20(e).

Here, deviation between the first patterns 2001 and 2003 and the second patterns 2002 and 2004 initially formed by DP is considered to be measured at a point in time in which the patterns 2005a to 2005h are formed. FIGS. 20(a) and 20(e) drawn in an upward direction (a z direction) of a wafer are the upper and lower drawings in FIG. 20(f). The lower drawing of FIG. 20(f) illustrates an aspect in which the eight patterns 2005a to 2005h corresponding to FIG. 20(e) are arranged side by side, but since all patterns have the same appearance, it is difficult to understand desirable patterns in which a distance therebetween is to be measured in order to measure deviation between the first and second patterns. In this regard, the attribute information related to the manufacturing process described above with reference to FIGS. 19(a) to 19(h) is considered in this example as well. In the upper drawing of FIG. 20(f), the first patterns 2001 and 2003 and the second patterns 2002 and 2004 are illustrated to the patterns 2005a to 2005h in the position in the x direction. In terms of a correspondence relation, for example, the pattern 2005a is a pattern shifting depending on the left edge position of the first pattern 2001. For this reason, the pattern 2005a is not a pattern formed directly by the manufacturing process of forming the left edge of the first pattern 2001 but a pattern in which its formation position depends on the manufacturing process of forming the first pattern 2001. Further, the pattern 2005b is a pattern in which its formation position depends on the manufacturing process of the right edge of the first pattern 2001. Similarly, for example, the pattern 2005c is a pattern in which its formation position depends on the manufacturing process of forming the second pattern 2002, and the pattern 2005d is a pattern in which its formation position depends on the manufacturing process of the right edge of the second pattern 2002. It is understood that when the attribute information is considered together, the deviation between the first and second patterns in the x direction can be evaluated, for example, based on a distance between a middle point (indicated by an x mark on an arrow indicating a width 2008) of the width 2008 between the right edge of the pattern 2005b and the left edge of the pattern 2005e and a middle point (indicated by an x mark on an arrow indicating a width 2009) of the width 2009 between the left edge of the pattern 2005c and the right edge of the pattern 2005d. In other words, for example, when the second pattern shifts rightwards (in the positive x direction) with respect to the first pattern, the middle point of the width 2009 shifts rightwards with respect to the middle point of the width 2008, and thus the deviation amount can be obtained by subtracting a design value of the distance between the middle points from the distance between the middle points on the image.

Similarly, it is understood that the deviation between the first and second patterns in the x direction can be evaluated, for example, based on a distance between a middle point of a width 2011 and a middle point of a width 2010 illustrated in FIG. 20(f), a distance between a middle point of a width 2012 and a middle point of a width 2013, or a distance between a middle point of a width 2014 and a middle point of a width 2015. The deviation may be measured using any one of a plurality of measurement points, or a stable deviation amount may be estimated by obtaining a plurality of measurement values using a plurality of measurement points and obtaining an average or median value thereof.

FIG. 20(g) illustrates attribute information of edges of the patterns 2005a to 2005h. IDs of the attribute information are indicated by alphabet letters (in this example, there are eight types of attributes A to D and a to d) in circles drawn on the respective edges. "A" denotes an attribute of a left edge of a sidewall spacer formed on a sidewall of a left edge of a pattern 2016 formed by the first manufacturing process, "B" denotes an attribute of a right edge of a sidewall spacer formed on a sidewall of a left edge of a pattern 2017 formed by the first manufacturing process, "a" denotes an attribute of a right edge of a sidewall spacer formed on a sidewall of a right edge of a pattern 2018 formed by the first manufacturing process, and "b" denotes an attribute of a left edge of a sidewall spacer formed on a sidewall of a right edge of a pattern 2019 formed by the first manufacturing process. Similarly, attributes C, D, c, and d are allocated to edges of sidewall spacers formed at sidewalls of patterns formed by the second manufacturing process according to the positions thereof as illustrated in FIG. 20(g). As described above, the attribute information of each edge can be extended to be decided according to information of another manufacturing process influencing the position of the edge or a positional relation between the edge and a pattern formed by a certain manufacturing process as well as information of the manufacturing process of directly forming the edge (for example, it is a left edge of a sidewall spacer formed on the left of a second pattern). The following rule can be derived for a combination of edges which may be used to evaluate the deviation between the first and second patterns based on the attribute information. First, edges having attributes of a capital letter and a lower-case letter representing the same alphabet letter are set as a pair, and a middle point thereof is considered. For example, a middle point of a width between an edge having an attribute A and an edge having an attribute a is referred to as a "middle point A-a." The deviation between the first and second patterns may be obtained based on a distance between either of the middle point A-a and a middle point B-b and either of a middle point C-c and a middle point D-d. In other words, (overlay deviation of second pattern on first pattern) (coordinates of middle point C-c or coordinates of middle point D-d)–(coordinates of middle point A-a or coordinates of middle point B-b)–(a design value of the distance between middle points). All the measurement points illustrated in FIG. 20(f) satisfy this condition, and for example, when the deviation is measured based on the distance between the middle point of the width 2008 and the middle point of the width 2009, the distance between the middle point A-a and the middle point C-c is measured. As described above, it is possible to obtain all combinations of edges used to measure the deviation using the attribute information.

Further, when design data is used as the layout information, and it is difficult to obtain design data (intent design data) of the final patterns 2005a to 2005h which are generated at the time of imaging and illustrated in the lower portion of FIG. 20(f), for example, intent design data is generated based on the patterns 2001 to 2004 which are design data of the previous process illustrated in the upper portion of FIGS. 20(f) and information of the manufacturing process illustrated in FIGS. 20(a) to 20(e). Attribute information is obtained based on the intent design data, and an EP or a measurement point in an EP is decided based on the intent design data and the attribute information. On the other hand, if there is intent design data but it is difficult to obtain design data of each process, attribute information is allocated to the intent design data based on information of each manufacturing process, and an EP or a measurement point in an EP is decided.

In this specification, the example of the overlay evaluation in which the attribute information is additionally considered, particularly, based on the example of between layers or the SADP have been described with reference to FIGS. 19(a) to 19(h) and 20(a) to 20(g). However, the present invention is not limited to this example, and can be used in another process such as an overlay evaluation in a device using self-aligned multi patterning (SAMP), directed self-assembly (DSA), a grid design, or the like. Further, the additional consideration of the attribute information is effective when a computer automatically decides an EP or a measurement point in an EP based on layout information, but it is very effective even when the user decides an EP or a measurement point in an EP manually other than automatically. It is because there are cases in which it is difficult to anticipate a formed edge and a manufacturing process of forming the edge based on layout information of a pattern to be finally formed. Further, even when it is possible to anticipate it, knowledge related to a process or specifying pattern position is necessary for anticipation. Thus, as the layout information and the attribute information are shown to the user through a GUI or the like, it helps the user when deciding an EP or a measurement point in an EP, and working efficiency can be significantly improved.

2.2.6 EP Decision Based on Divisional Imaging

In the step (step 105 or step 111 in FIG. 1) of deciding the evaluation point, when the overlay position in the x direction is evaluated, first and second evaluation points are decided so that at least one of right and left edges of the first pattern and one of right and left edges of the second pattern are included in the first evaluation point, and one of the right and left edges of the first pattern and one of the right and left edges of the second pattern are included in the second evaluation point, and the overlay deviation is evaluated using the first and second evaluation points. Here, a direction of a pattern included in the first evaluation point and a direction of a pattern edge included in the second evaluation point are reversed right and left in the first and second patterns.

Similarly, when the overlay position in the y direction is evaluated, first and second evaluation points are decided so that at least one of upper and lower edges of the first pattern and one of upper and lower edges of the second pattern are included in the first evaluation point, and one of the upper and lower edges of the first pattern and one of the upper and lower edges of the second pattern are included in the second evaluation point, and the overlay deviation is evaluated using the first and second evaluation points. Here, a direction of a pattern edge included in the first evaluation point and a direction of a pattern edge included in the second evaluation point are upside-down in the first and second patterns.

Figure 21:
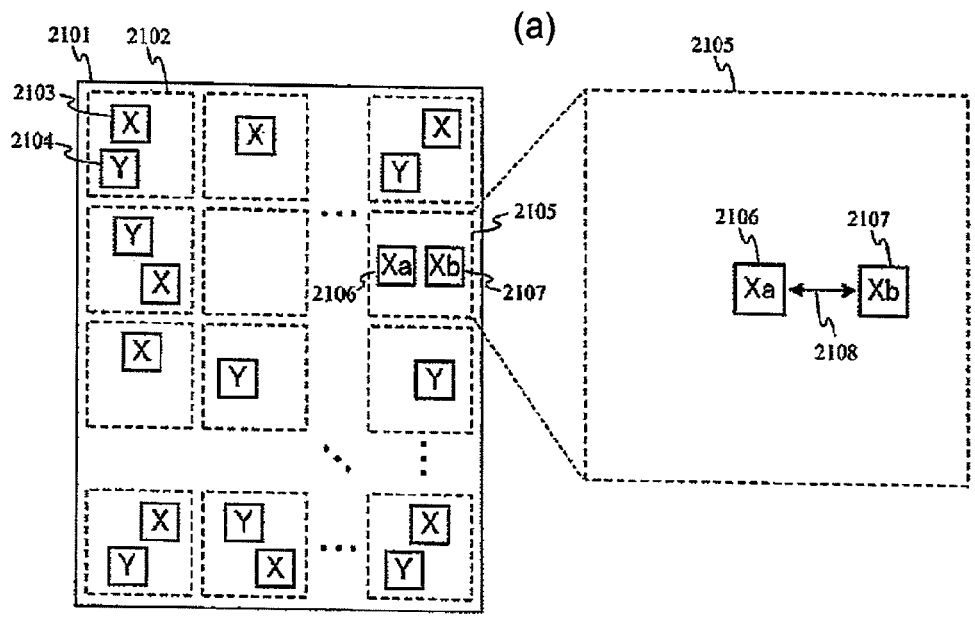
FIGS. 21(a) to 21(c) are diagrams illustrating a method of measuring a deviation amount based on two evaluation points.
Figure 21:
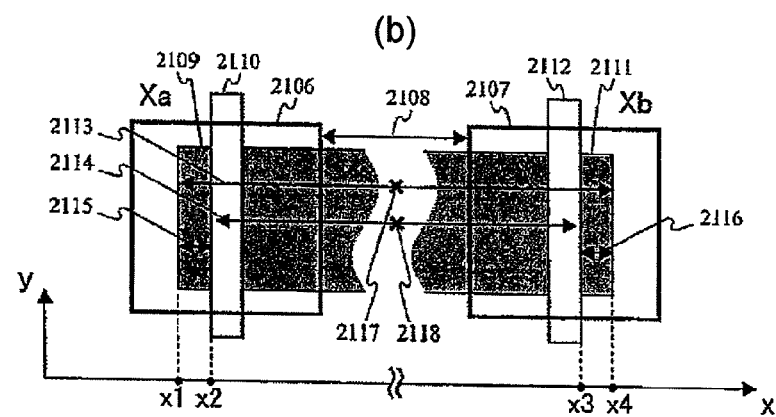
Figure 21:
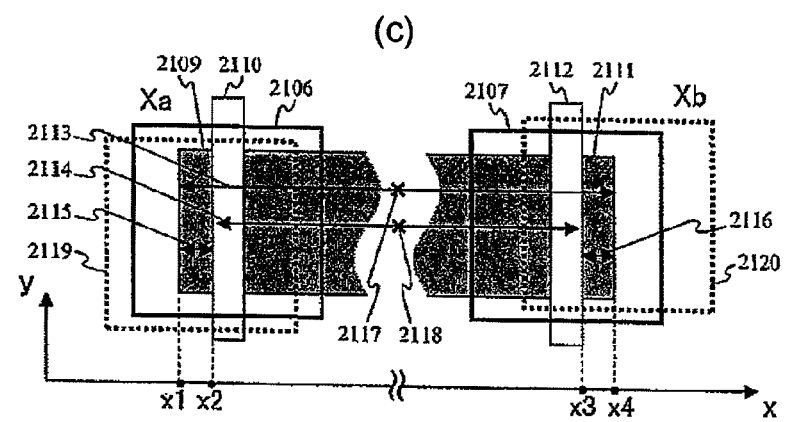

This feature will be further described. When the overlay evaluation is performed using a normal circuit pattern other than an overlay evaluation-dedicated pattern, it depends on a pattern layout whether there is an EP including a pattern suitable for overlay evaluation, and there is not necessarily a desired EP. For this reason, when the in-plane distribution of the overlay deviation is evaluated using an actual pattern, how to extract many EPs without imbalance is a problem, and the present processing is effective to this problem. First, as described above with reference to FIGS. 7(a) to 7(d), as an example of an EP selection evaluation criterion, there is "(B) when the overlay position in the x direction is evaluated, both right and left edges of a pattern are included in the respective evaluation points, and when the overlay direction in the y direction is evaluated, both upper and lower edges of a pattern are included in the respective evaluation points," but in some cases, there are little EP in which all of a group of edges necessary for measurement are included in a field of view depending on a pattern layout. A left view of FIG. 21(a) is an example in which an EP is extracted in a chip 2101, and a dotted frame indicating an area 2102 represents an area (corresponding to the area 907 of FIG. 9(b)) in which an EP is extracted, an EP 2103 in which "x" is written in a square represents an EP (referred to as an "EPX" and corresponding to the EP 910 of FIG. 9(b)) in which only the overlay deviation in the x direction can be evaluated, and an EP 2104 in which "y" is written in a square represents an EP (referred to as an "EPY" and corresponding to the EP 911 of FIG. 9(b)) in which only the overlay deviation in the y direction can be evaluated. Among the dotted frames, there are a dotted frame including no EP and a dotted frame including only an EPX or an EPY. On the other hand, a method of increasing a possibility that there will be an EP satisfying the criterion by lowering an imaging magnification of an EP and increasing a field of view of an EP so that many patterns are included in a field of view is considered. Here, since the imaging magnification and the measurement accuracy are in the trade-off relation, there is a limitation to increasing a field of view. In this regard, instead of estimating overlay deviation based on a single EP, a method of estimating a deviation amount based on two EPs is considered. In other words, there are cases in which when a group of edges necessary for evaluation of overlay deviation which are not included in a field of view in a single EP are divided into a first EP and a second EP and then imaged, all of a group of edges can be included in a field of view. For example, in FIG. 21(a), no EP in which the overlay deviation can be evaluated in a single EP was present in a dotted frame 2105, but there are cases in which as divisional imaging is allowed, EPs can be set as illustrated in FIG. 21(a). In FIG. 21(a), a first EP 2106 (referred to as an "EPXa") including a pattern edge changing in the X direction and a second EP 2107 (referred to as an "EPXb") can be set, and it is possible to evaluate the overlay deviation in the X direction which is hardly evaluated in the related art based on imaged images of both the EPs. A right view of FIG. 21(a) is an enlarged view of the area 2105 in which EPXa and EPXb can be set. Although not illustrated, similarly, there may be also cases in which EPYa and EPYb can be set as two EPs in which the overlay deviation in the Y direction can be evaluated, and EPa and EPb can be set as two EPs in which the overlay deviation in the X and Y directions can be evaluated.

Here, it is discovered that in order to prevent a deviation measurement value from being affected by an increase/decrease in a pattern width or imaging deviation of two EPs, it is necessary to image a group of edges necessary for measurement in the first EP and the second EP by the above-described combination. FIG. 21(b) illustrates examples of the first and second EPs satisfying the above-described combination. In order to evaluate the overlay deviation in the x direction between first patterns 2109 and 2111 (indicated by hatched patterns) formed on a lower layer and second patterns 2110 and 2112 (indicated by white patterns) formed on an upper layer, at least one of the right and left edges of the first pattern and one of the right and left edges of the second pattern need to be included in the first EP, and in this example, the left edge of the first pattern 2109 and the left edge of the second pattern 2110 are included. Further, one of the right and left edges of the first pattern and one of the right and left edges of the second pattern need to be included in the second EP, and in this example, the right edge of the first pattern 2111 and the right edge of the second pattern 2112 are included. In addition, a direction of a pattern included in the first EP and a direction of a pattern included in the second EP need to be reversed right and left in the respective first and second patterns. When a direction of a pattern is defined as a direction from the inside of the pattern to the outside, in this example, both the left edge of the first pattern 2109 and the left edge of the second pattern 2110 which are measurement target edges of the first EP are in the right direction, both the right edge of the first pattern 2111 and the right edge of the second pattern 2112 which are measurement target edges of the second EP are in the right direction, and thus a condition in which a direction is reversed is satisfied for the first and second patterns. In this example, the deviation between the first and second patterns can be evaluated by subtracting a design value of the distance between middle points from a distance between a middle point 2117 of a width 2113 between the left edge (the x coordinate of the edge position is denoted by x1) of the first pattern 2109 and the right edge (the x coordinate of the edge position is denoted by x4) of the first pattern 2111 and a middle point 2118 of a width 2114 between the left edge (the x coordinate of the edge position is denoted by x2) of the second pattern 2110 and the right edge (the x coordinate of the edge position is denoted by x3) of the second pattern 2112. In this example, the design value of the distance between the middle points is assumed to be 0. When the overlay deviation is converted into an equation, the following equation is obtained.

$$\text{(overlay deviation of second pattern on first pattern)} =$$
$$\text{(middle point of width 2114)} - \text{(middle point of width 2113)} =$$
$$(x2 + x3)/2 - (x1 + x4)/2 =$$
$$((x2 - x1) - (x4 - x3))/2 = ((\text{width 2115}) - (\text{width 2116}))/2$$

In other words, since the overlay deviation is obtained by the difference between the width 2115 between the left edge of the pattern 2109 and the left edge of the pattern 2110 in the first EP and the width 2116 between the right edge of the pattern 2111 and the right edge of the pattern 2112 in the second EP, when the measurement target edge is in a field of view of each EP, a correct measurement value can be obtained even when the imaging position of each EP slightly deviates. FIG. 21(c) illustrates an example of actual imaging position, but actual imaging positions 2119 and 2120 of EPXa and EPXb indicated by dotted frames deviate from imaging positions 2106 and 2107 of EPXa and EPXb indicated by thick lines at the time of setting. As imaging is performed twice as described above, a relative imaging position between EPXa and EPXb is likely to deviate, but since the deviation of the imaging position does not directly affect the measurement value of the overlay deviation as described above, it is possible to correctly obtain the overlay deviation when it is possible to correctly measure the widths 2115 and 2116 from the respective images.

Further, the obtained overlay deviation is hardly affected by an increase/decrease in a pattern width due to the same reason as the content described above with reference to FIGS. 7(a) to 7(d). However, this may be obtained only when the same degree of shape deformation occurs in the patterns 2110 and 2112 (or the patterns 2109 and 2111) (here, a pattern including an edge to be measured is referred to as a "measurement target pattern"). For example, although the overlay deviation does not occur, when the measurement target pattern 2110 increases to be much thicker than the measurement target pattern 2112, the overlay deviation occurs in a calculation. In order to cause a pair of measurement target patterns 2110 and 2112 (or a pair of measurement target patterns 2109 and 2111) to have the same degree of shape deformation, the shape of the measurement target pattern or the shape of a pattern around each measurement target pattern needs to be similar to the shape of the other pattern configuring a pair, and needs to be considered when an EP is set. The reason why similarity of the shape of the surrounding pattern is also considered is because there are cases in which the shape of a surrounding pattern affects the shape of the measurement target pattern due to an optical proximity effect at the time of pattern exposure. Further, in order to cause the measurement target patterns to have the same degree of shape deformation, a pair of measurement target patterns needs to have a similar manufacturing condition. In addition, since the overlay deviation is calculated using a pair of measurement target patterns, the same degree of overlay deviation has to occur in a pair of measurement target patterns. In view of this point, a pair of measurement target patterns needs to be closely arranged, and to this end, the first and second EPs need to be closely arranged. At the time of EP decision, a constraint condition can be set to the distance (a distance 2108 in FIGS. 21(a) to 21(c)) between EPs.

As two EPs are imaged to measure a single deviation amount as described above, the throughput of measurement decreases, but alternatives of EPs satisfying a measurement criterion increase, and a close in-plane deviation distribution is likely to be estimated without imbalance.

2.3 Measurement Point/Processing Method Decision

According to the present invention, in the step (step 105 or step 111 in FIG. 1) of deciding the evaluation point, a measurement point used to evaluate the overlay position in the evaluation point is decided based on the pattern layout information. Further, similarly, the step of deciding the evaluation point includes a process of deciding a processing method of evaluating an overlay position in the evaluation point based on the pattern layout information for each evaluation point, and alternatives of the processing method include at least a method of imaging the evaluation point, comparing an obtained image with design data, and evaluating an overlay position (the processing method A) and a method of imaging the evaluation point, recognizing a pattern from an obtained image by image processing, and evaluating an overlay position (the processing method B).

This feature will be further described. Although there are a plurality of patterns in a decided EP, it is necessary to measure a distance between the first pattern and the second pattern for the overlay evaluation. According to circumstances, there are cases in which all patterns are used for measurement of the distance, but, for example, distance measurement may be performed excluding a position at which pattern deformation is likely to occur as described above. For this reason, the measurement point is decided for each evaluation pattern based on the layout information.

Furthermore, the processing method of obtaining the distance may be decided for each evaluation pattern. The process using design data such as the processing method A and the process of obtaining a measurement value directly from an image such as the processing method B have advantages and disadvantages according to a pattern included in an EP, it is effective to decide the processing method for each EP based on the layout information.

The measurement point and the processing method will be described using two kinds of EPs illustrated in FIGS. 11(a) and 11(b) as an example. In an EP 1101 of FIG. 11(a), first patterns formed by first exposure are indicated by patterns (for example, 1102) hatched by oblique lines, and second patterns formed by second exposure are indicated by white patterns (for example, 1103). In order to evaluate the overlay position between the first pattern and the second pattern, for example, a method of setting two positions indicated by arrows 1104 and 1105 as the measurement points, recognizing the positions by image processing, and measuring the distance between the first pattern and the second pattern at the corresponding positions is considered. This method belongs to the processing method B. However, the pattern in the EP 1101 is complicated, and advanced image processing is necessary in order to recognizes the positions of the arrows 1104 and 1105 and perform the measurement. At this point of view, the processing method A is suitable for the evaluation in the EP 1101. In other words, matching between each of design data (referred to as "first design data") for first exposure and design data (referred to as "second design data") for second exposure and a pattern in an imaged image is performed. It is possible to evaluate the overlay deviation based on deviation between the matching position of the first design data and the matching position of the second design data. Alternatively, the first pattern in the imaged image is recognized by matching of the first design data, the second pattern in the imaged image is similarly recognized by matching of the second design data, and the overlay deviation can be evaluated based on the positional relation between the recognized first pattern and the second pattern.

Meanwhile, in an EP 1106 of FIG. 11(b), a first pattern 1107 and a second pattern 1108 are arranged side by side. As an example of image processing for performing the overlay evaluation in the x direction using this EP, a technique of detecting right and left edges (edges included in dotted frames 1110) in the first and second patterns and measuring a distance 1109 between the two patterns as an evaluation point is considered. As an example of a method of detecting the right and left edges, it is desirable to create a brightness profile 1111 by accumulating brightness values of an imaged image in the y direction and detects a portion in which a brightness value remarkably changes (many electrons are emitted from an edge portion of a pattern and becomes bright on an image). As described above, in the EP 1106, the overlay evaluation can be performed by simple image processing without using design data, and thus the processing method B is appropriate.

On the other hand, in the step of deciding an EP, the user can designates the processing method (for example, the processing method A or the processing method B) for obtaining the distance in advance, and an area in which the measurement value can be obtained by the processing method can be selected as an EP based on the layout information. Particularly, in processing of the processing method B, design data need not be used, and thus there may be the user who desires to select only an area in which processing of the processing method B is possible as an EP. In this case, at the time of recipe generation, for example, an EP is decided using design data, but there is a merit that it is unnecessary to handle design data at the time of imaging/measurement using a scanning charged particle microscope.

2.4 Overlay Deviation Vector Calculation

According to the present invention, in the step (step 105 or step 111 in FIG. 1) of deciding the evaluation point, a plurality of evaluation points in which a direction in which an overlay position is evaluable is decided for each evaluation point are decided, and in the step (step 113 in FIG. 1) of evaluating the overlay position, an overlay deviation vector at certain coordinates is calculated based on overlay deviation in a direction in which the overlay position is evaluable which is measured in each of the plurality of evaluation points.

Figure 16:
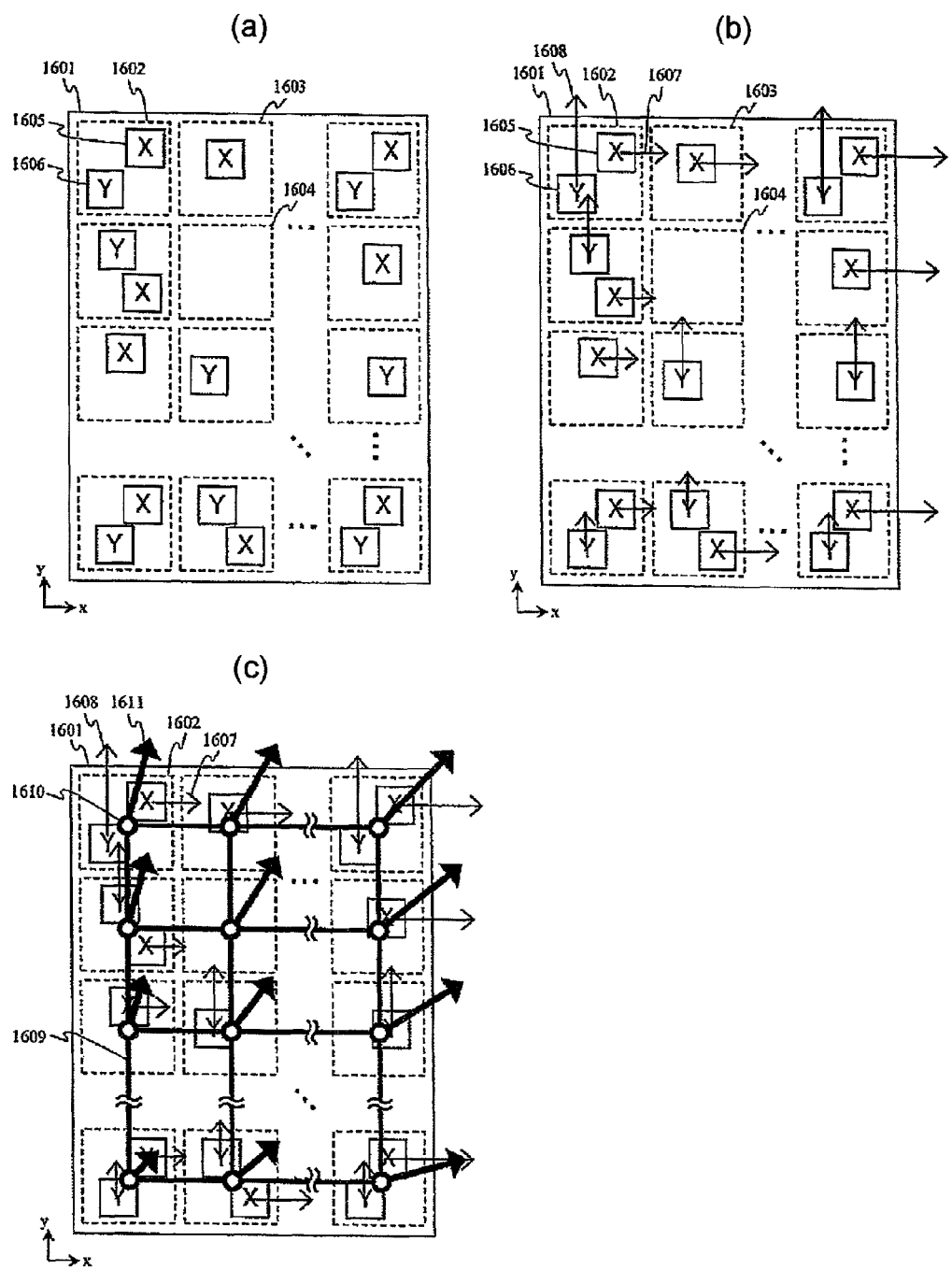
FIGS. 16(a) to 16(c) are diagrams illustrating a method of evaluating an in-plane distribution of a deviation vector.

This feature will be further described. When the overlay evaluation is performed using a normal circuit pattern instead of an overlay evaluation-dedicated pattern, it depends on a pattern layout whether there is an EP including a pattern suitable for an overlay evaluation, and there is not necessarily a desired EP. For this reason, when the in-plane distribution of the overlay deviation is evaluated using an actual pattern, it is consequential how to calculate information effective for estimation of the in-plane distribution of the overlay deviation even when the number of EPs which can be extracted is small. FIG. 16(a) illustrates an example in which an EP is extracted from a chip 1601, and a dotted frame indicated by an area 1602 represents an area (corresponding to the area 907 of FIG. 9(b)) in which an EP is extracted, an EP 1605 in which "x" is written in a square represents an EP (referred to as "EPX" and corresponding to the EP 910 of FIG. 9(b)) in which only the overlay deviation in the x direction can be evaluated, and an EP 1606 in which "y" is written in a square represents an EP (referred to as "EPY" and corresponding to the EP 911 of FIG. 9(b)) in which only the overlay deviation in the y direction can be evaluated. Areas such as 1602 in which an EP is extracted have to be arranged centering on coordinates at which extraction is desired to be performed, and, for example, when a reliable overlay deviation distribution tendency is desired to be understood by extracting EPs at certain intervals without imbalance, an EP extraction area needs to be set at certain intervals in a grid form as illustrated in FIG. 16(a). However, even when an EP search is performed in areas arranged in the grid form, there are cases in which no EP is present nearby the center of the area 1602 as in the area 1602 and an EP is extracted at an end of the area 1602 such as an EP 1605, cases in which no EP is present at all as in an area 1604, or cases in which only EPX is present as in an area 1603. FIG. 16(b) illustrates a result of imaging the extracted EPs on such an imbalanced EP extraction result and calculating the overlay deviation. In FIG. 16(b), the magnitude of an overlay deviation amount calculated from an image obtained by imaging each EP is indicated by an arrow extending from each EP, and a direction of an arrow represents a direction of overlay deviation which can be measured in each EP. For example, an arrow 1607 representing deviation in the x direction extends from the EP1605 in which the overlay deviation in the x direction can be measured. Similarly, an arrow 1608 representing deviation in the y direction extends from the EP1606 in which the overlay deviation in the y direction can be measured. However, it is difficult to understand the deviation distribution tendency based on a group of imbalanced overlay deviation arrows of respective directions in FIG. 16(b). In this regard, in the present invention, an interpolation process of the measurement value is performed based on a group of overlay deviation arrows (for example 1607 and 1608) of the respective directions illustrated in FIG. 16(b), and a two-dimensional deviation vector (for example, 1611) (in the x and y directions) is estimated at desired coordinates as illustrated in FIG. 16(c). Even when the EP distribution is sparse or imbalance, it is possible to closely estimate the in-plane deviation distribution without imbalance to some extent. In FIG. 16(c), a grid pattern 1609 indicated by a thick line is illustrated, and a thick circle (for example, 1610) present at a crossing point of a grid represents coordinates on a chip at which the overlay deviation is desired to be obtained. A thick arrow extending from the thick circle represents a vector (for example, 1611) indicating the overlay deviation in the thick circle. As a method of obtaining a vector indicating the overlay deviation in the thick circle from a group of overlay deviation arrows of the respective directions, for example, the deviation amount in the x direction in each thick circle is obtained from a group of overlay deviation arrows in the x direction such as 1607 by interpolation (a concrete example of an interpolation method will be described later with reference to FIGS. 18(a) to 18(c)), and similarly, the deviation amount in the y direction in each thick circle is obtained by interpolation from a group of overlay deviation arrows in the y direction such as 1608. When the deviation amounts in the x and y directions in each thick circle are obtained, a two-dimensional deviation vector (for example, 1611) having the obtained deviation amount as components in each thick circle is given.

In FIG. 16(c), the user can arbitrarily set coordinates at which the overlay deviation indicated by the thick circle is desired to be obtained, overlay deviation, intervals of a grid 1609 may be more finally set to obtain close deviation distribution, an intervals of a grid may be irregularly changed, and thick circles may be arranged arbitrarily instead of a grid form.

Figure 17:
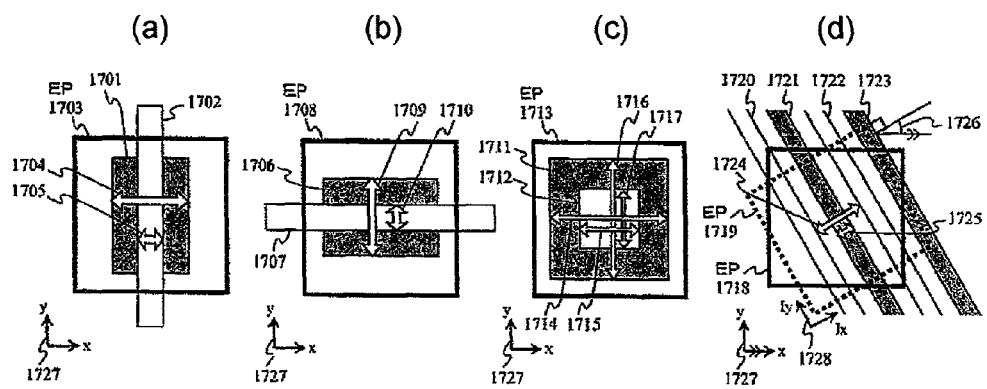
FIGS. 17(a) to 17(d) are diagrams illustrating a variation of an evaluation point.

Further, in the example illustrated in FIGS. 16(a) to 16(c), only an EP in which the overlay deviation of each direction can be evaluated from a single EP is extracted, but an EP in which the overlay deviation of each direction can be evaluated from two EPs described above with reference to FIGS. 21(a) to 21(c) may be included. Furthermore, in the example illustrated in FIGS. 16(a) to 16(c), two kinds of EPs, that is, an EPX in which only the overlay deviation in the x direction can be evaluated and an EPY in which only the overlay in the y direction deviation can be evaluated are extracted, but similar processing can be performed even on any other kind of EP related to a measurable direction, and it can be used for estimation of a two-dimensional deviation vector. FIGS. 17(a) to 17(d) illustrate a variation of an EP related to a measurable direction. Patterns 1701, 1706, 1711, 1721, and 1723 hatched by oblique lines are first patterns, and white patterns 1702, 1707, 1712, 1720, and 1722 are second patterns, and thick frames 1703, 1708, 1713, and 1718 indicate EPs. From widths 1704, 1709, 1714, 1716, and 1725 of the first patterns and widths 1705, 1710, 1715, 1717, and 1724 of the second patterns, the overlay deviation in the x direction can be evaluated in an EP 1703, the overlay deviation in the y direction can be evaluated in an EP 1708, the overlay deviation in the x and y directions can be evaluated in an EP 1713, and the overlay deviation in a direction of an angle 1726 can be evaluated in an EP 1718. An oblique interconnection which is oblique at the angle 1726 is present in a field of view of the EP 1718, and thus the overlay deviation in the direction of the angle 1726 can be evaluated, but when the angle 1726 is 0°, the EP 1718 is an EPX, and when the angle 1726 is 90°, the EP 1718 is an EPY. Further, when the patterns illustrated in FIG. 17(d) are imaged by an SEM, in order to vividly image a pattern edge, a scanning direction of electron beams can be set vertically to an edge, and a dotted frame 1719 obtained by rotating the EP 1718 leftwards by the angle 1726 can be used as an EP. In this case, a coordinate system 1728 (referred to as an "Ix-Iy coordinate system") representing the x and y directions on an image is rotated from a coordinate system 1727 (referred to as an "x-y coordinate system") of a wafer, a shot, or a chip by the angle 1726. Thus, the overlay deviation in the Ix direction obtained on the image is the overlay deviation of the direction of the angle 1726 in the x-y coordinate system. As described above, information of overlay deviation in an arbitrary direction in each EP can be used for estimation of a two-dimensional deviation vector.

Here, since reliability of the measurement value obtained by the interpolation process is not necessarily high, estimation reliability is calculated for each estimated deviation vector. When a deviation evaluation result is fed back to a semiconductor manufacturing device or the like to correct the deviation, a degree of adding a deviation vector can be controlled according to the reliability. As a method of calculating the reliability, a difference between interpolation and extrapolation in an interpolation process, a distance between an EP serving as an interpolated point and an interpolation point, or the like may be used. FIG. 18(a) illustrates a deviation interpolation process. In this example, overlay deviation 1811 in the x direction in a thick circle 1810 and overlay deviation 1813 in the x direction in a thick circle 1812 are inferred from overlay deviation 1804 to 1806 in the x direction measured in three EPXs 1801 to 1803 by an interpolation process. The thick circles 1810 and 1812 represent coordinates on a chip designated to obtain overlay deviation by the user, similarly to the thick circle 1610. Examples of the interpolation process include linear interpolation and curved surface interpolation. Since the thick circle 1810 is present in an area surrounded by dotted lines 1807 to 1809 connecting the EPs 1801 to 1803 serving as interpolated points, the vector 1811 can be estimated by the interpolation process, and it is generally high in estimation reliability. However, since the thick circle 1812 is outside the area surrounded by the dotted lines 1807 to 1809, the vector 1813 is estimated by the extrapolation process, and it is generally low in estimation reliability. Further, the estimation reliability may be estimated consecutively instead of simply using two processes of interpolation and extrapolation. For example, as illustrated in FIG. 18(b), similarly to FIG. 18(a), overlay deviation 1815, 1818, and 1821 in the x direction in thick circles 1814, 1817, and 1820 on interpolated points 1801 to 1803 are considered to be estimated. The estimations of all the deviation vectors in the thick circles are performed by the extrapolation process since the thick circles are outside an area surrounded by dotted lines 1807 to 1809, but not the same in the estimation reliability. For example, vertical lines from the thick circles 1814, 1817, and 1820 to a straight line 1809 connecting an EP 1801 and an EP 1803 serving as interpolated points are considered, and the lengths of the vertical lines are assumed to be 1816, 1819, and 1922. When the lengths 1816 and 1819 of the vertical lines are compared, the length 1816 is shorter. Thus, from a point of view of a distance from the area surrounded by the interpolated points, an estimation vector 1815 is considered to be higher in estimation reliability than an estimation vector 1818. Meanwhile, when the lengths 1816 and 1822 of the vertical lines are compared, the length 1822 is shorter, but an estimation vector 1821 is not necessarily higher in estimation reliability than the estimation vector 1815. When crossing points 1823 and 1825 between the vertical lines and the straight line 1809 are compared, the crossing point 1823 is present between the interpolated points 1801 and 1803, but the crossing point 1825 is present outside between the interpolated points 1801 and 1803. Thus, from a point of view in which an interpolation point is present between interpolated points in connection with the direction of the straight line 1809, the estimation vector 1815 is considered to be higher in estimation reliability than the estimation vector 1821. The above-described reliability calculating method is an example, and the present invention is not limited to this example. For example, a technique of finding an interpolated point closest to an interpolation point and using a distance between the interpolation point and the interpolated point for a reliability calculation may be considered.

Figure 18:
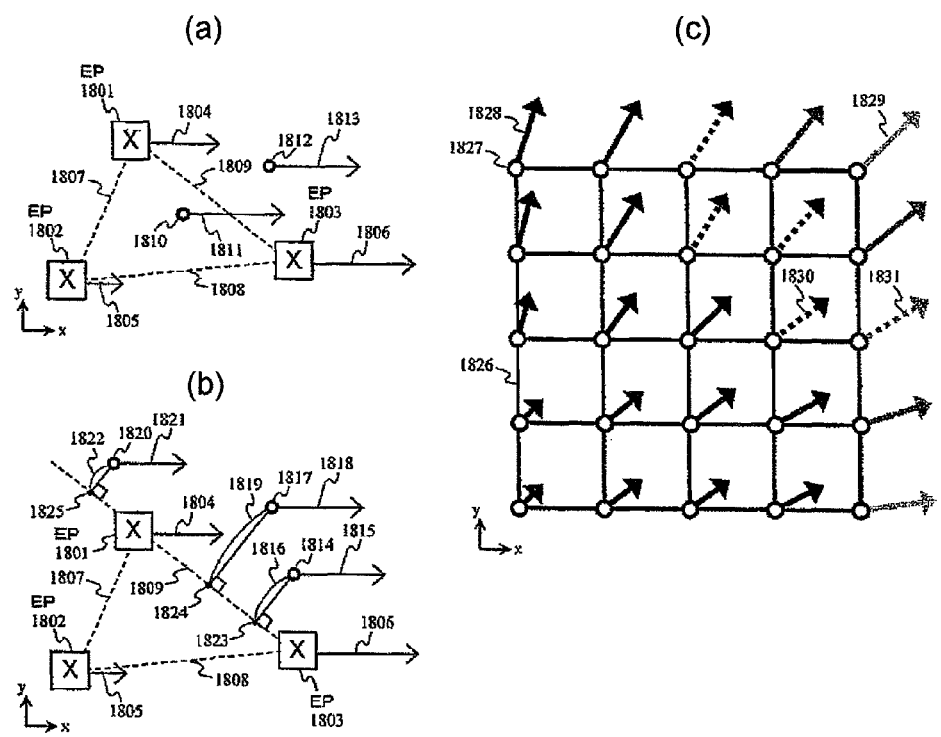
FIGS. 18(a) to 18(c) are diagrams illustrating a method of calculating and displaying reliability of a deviation vector.

FIG. 18(*c*) illustrates an example of a distinction between interpolation and extrapolation of an estimation vector and a method of displaying estimation reliability. A thick circle (for example, 1827) present at a crossing point of a grid pattern 1826 represents coordinates on a chip at which overlay deviation is desired to be obtained, and an arrow extending from the thick circle is a vector (for example, 1828 to 1831) representing overlay deviation in the thick circle which is estimated by interpolation. A solid line vector (for example, 1828 and 1829) is a vector obtained by the interpolation process, and a dotted line vector (for example, 1830 and 1831) is a vector obtained by the extrapolation process. Further, brightness of a vector represents reliability, and for example, for the vectors estimated by the interpolation process, a gray vector 1829 is lower in estimation reliability than a black vector 1828. Similarly, for the vectors estimated by the extrapolation process, a gray vector 1831 is lower in estimation reliability than a black vector 1830. There may be several brightness levels in connection with reliability, and a numerical value indicating quantified reliability may be displayed beside each vector.

3. GUI

Figure 12:
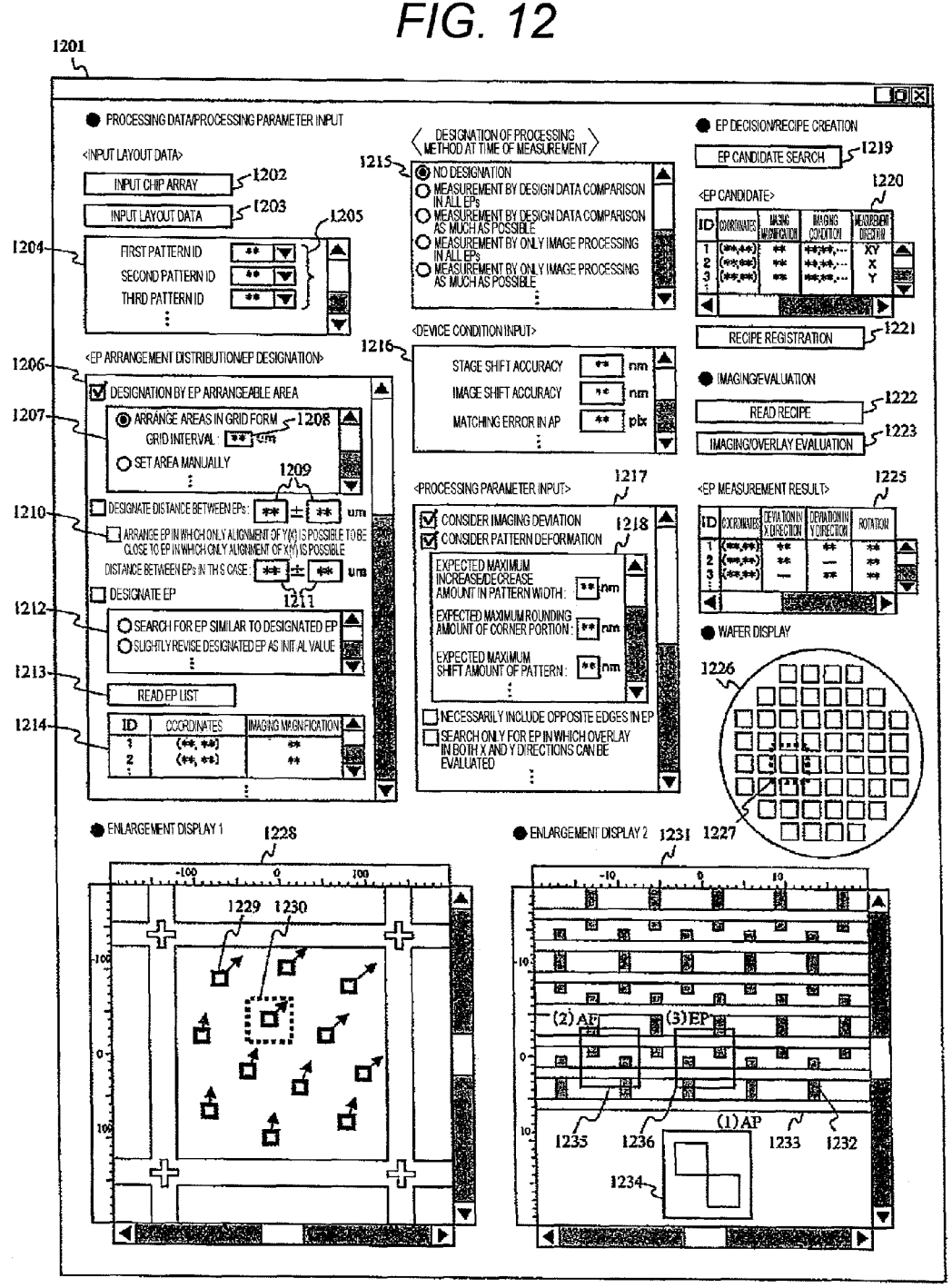
FIG. 12 is a diagram illustrating a GUI according to the present invention.

FIG. 12 illustrates an example of a GUI for performing an input of various kinds of information, recipe creation/output setting or display, and SEM device control according to the present invention. Various kinds of information rendered in a window 1201 of FIG. 12 may be displayed on a single screen or may be divided and displayed on a display.

A layout data input (step 102) method will be described. A chip array may be input by pushing a button 1202. Further, layout data may be input by pushing a button 1203. As layout data, layout data of the first pattern and layout data of the second pattern may be input as different files, or merged data may be input. Particularly, when a design data file is input as layout data, there are cases in which information of stacked layers may be included. In this regard, in a window 1204, a first pattern and a second pattern which are subject to overlay evaluation can be designated using an ID or the like. In the case of overlay evaluation between layers, the first pattern and the second pattern are designated using layer IDs, and in the case of overlay evaluation of DP, the first pattern and the second pattern are designated using exposure IDs, for example, a pull-down menu 1205. Further, the number of patterns which are subject to overlay evaluation may be three or more.

As an example of an EP selection condition input (step 103), a method of designating an EP arrangement distribution or an EP will be described. In a window 1206, when a check box of "designation by EP arrangeable area" is set to ON, the EP decision described above with reference to FIGS. 9(*a*) and 9(*b*) can be performed. In this case, a method of setting an EP arrangeable area can be selected from among "arrange area in grid form," "manually set area," and the like through a radio button in a window 1207. When "arrange area in grid form" is selected, a grid interval at which areas are arranged can be designated in a box 1208. Besides, although not illustrated in FIG. 12, it is possible to designate the number of areas, the width of an area, between areas, and an area arrangement method other than a grid form.

When a check box of "designate distance between EPs" is set to ON in the window 1206, the EP decision described above with reference to FIGS. 9(*c*) and 9(*d*) can be performed. In this case, a distance between EPs can be designated in a box 1209. Further, when a check box 1210 is set to ON, an EP search can be performed so that an EP (EPY) in which only the overlay evaluation in the y direction can be performed is arranged to be close to an EP (EPX) in which only the overlay evaluation in the x direction can be performed as much as possible (in contrast, an EPX is arranged to be close to an EPY). At this time, a distance between an EPX and an EPY can be designated in a box 1211.

When a check box of "designate EP" is set to ON in the window 1206, the EP designation described above with reference to FIGS. 10(*a*) and 10(*b*) can be performed. In this case, "search for EP similar to designated EP" and "slightly revise designated EP as initial value" can be selected using a radio button in a window 1212. Further, an EP may be designated using a mouse or the like in one of displays 1226, 1228, and 1231 which will be described later, or an EP may be designated by a list file read by pushing a button 1213. A list of designated EPs is displayed on a list 1214, and an EP to be actually used as a designated EP may be re-designated on the same list.

As an example of an EP selection condition input (step 103), a method of designating a processing method at the time of measurement will be described. In a window 1215, the processing method (the processing method A or the processing method B) for evaluating the overlay position described above with reference to FIGS. 11(*a*) and 11(*b*) can be designated using a radio button or the like, and an EP satisfying the designated condition can be decided. Examples of the designation method include "no designation," "measurement by design data comparison in all EPs," "measurement by design data comparison as much as possible," "measurement by only image processing in all EPs," and "measurement by only image processing as much as possible."

As an example of a device condition input (step 104), a method of inputting a device condition will be described. In a window 1216, assumed stage shift accuracy, image shift accuracy, a matching error in an AP, and the like can be input, and used for estimation of estimation imaging deviation at the time of EP decision or the like.

As an example of a processing parameter (step 101), a method of inputting a processing parameter at the time of EP decision will be described. As each check box is set to ON in a window 1217, at the time of EP decision, "consider imaging deviation (described above with reference to FIGS. 5(*a*) to 5(*d*))," "consider pattern deformation (described above with reference to FIGS. 6(*a*) to 6(*d*))," "necessarily include opposite edges in EP (described above with reference to FIGS. 7(*a*) to 7(*d*))," "search for only EP in which overlay in x and y directions can be evaluated (described above with reference to FIGS. 9(*a*) to 9(*d*))," or the like can be performed. Further, although not illustrated, designation such as "consider invisibility of lower layer pattern by upper layer pattern" described above with reference to FIGS. 8(*a*) to 8(*e*) can be performed. When "consider pattern deformation" or "consider invisibility of lower layer pattern by upper layer pattern" is selected, in a window 1218, parameters such as "expected maximum increase/decrease amount in pattern width," "expected maximum rounding amount of corner portion," and "expected maximum shift amount of pattern" can be input, and deformation or invisibility can be estimated based on the input parameters.

As a button 1219 is pushed, it is possible to search for an EP candidate based on an input of the layout data, the processing parameter, or the like and display a result. In the present invention, the EP candidate can be displayed together with the EP attribute information. This display will be further described. In EP decision, it is effective to show a plurality of EP candidates to the user and enable the user to select an EP candidate from among the EP candidates, instead of automatically selecting all EPs. As a method of giving the user determination information for EP selection, positions of EPs on a wafer may be plotted and displayed in order to understand an in-plane distribution of EPs. Further, the attribute information of the EP candidate may be displayed, and examples of the attribute information include (A) allowable imaging deviation/estimation imaging deviation, (B) an imaging sequence/imaging condition/assumed imaging period of time, (C) deformation easiness of pattern used as a reference of evaluation stability, (D) invisibility of a pattern or invisibility easiness by deformation of a pattern, (E) a processing method of an evaluating measurement point/overlay position, and (F) a direction of an evaluable overlay position. The direction of the evaluable overlay position of (F) is information representing that only an overlay position in the X direction or the Y direction is evaluable, that overlay positions in the X and Y directions are evaluable, or that an overlay position in an A° direction is evaluable (A is an arbitrary real number, A=0 for EPX, and A=90 for EPY). For example, when only a pattern edge changing in the X direction is included in an EP candidate, it is difficult to evaluate the overlay position in the Y direction. This information can be obtained by analyzing the layout information of the EP candidate. This information may be displayed as a numerical value or a diagram, and, for example, a list of EP candidates may be displayed on a list 1220. In the same list, various kinds of attribute information as well as EP coordinates, the imaging magnification, the imaging condition, the overlay evaluable direction (a distinction among EPXY, EPX, and EPY) can be displayed. Further, the attribute information related to an EP position or each EP can be displayed on the displays 1226, 1228, and 1231. Although all pieces of attribute information are not illustrated on the displays 1226, 1228, and 1231, any attribute information can be converted into a numerical value or a figure and then displayed. The display 1226 illustrates a wafer, and as a range 1227 is designated in the display 1226 using a mouse or the like, the corresponding range can be enlarged and displayed on the display 1228. In the display 1228, the position of the EP candidate is indicated by a thick frame (for example, a thick frame 1229), and after the overlay deviation amount is measured, the deviation amount can be displayed using a vector (for example, an arrow extending from the thick frame 1229). Further, as a range 1230 is designated in the display 1228 using a mouse or the like, the corresponding range can be enlarged and displayed on the display 1231. In the display 1231, as the pattern layout information, the first patterns are displayed as patterns (for example, 1232) hatched by oblique lines, the second patterns are displayed as white patterns (for example, 1233), and further, an EP 1236 and an imaging sequence for imaging the corresponding EP are displayed. In this example, first, addressing is performed through an AP 1234, then auto-focusing is performed through an AF 1235, and lastly, an imaging sequence for imaging the EP 1236 is set. In FIG. 12, the imaging sequence is written as numbers (1) to (3) written before notations of AP, AF, and EP. For example, though an EP position is not displayed on the display 1226, this is a display example, and layout information, an EP position, an imaging sequence, an imaging condition, a measurement point/processing method, an overlay evaluation result, or the like can be arbitrarily displayed on the display 1226, 1228, or 1231.

As a button 1221 is pushed, a decided EP, an imaging sequence, an imaging condition, a measurement point/processing method, or the like can be registered to a recipe. At this time, in the list 1220 or the displays 1226, 1228, and 1231, an EP to be actually registered to a recipe can be re-designated from among the EP candidates.

Then, as a button 1222 is pushed, a recipe to be used is designated (a previously registered recipe may be used or a recipe created in the past may be used). As a button 1223 is pushed, an imaging/overlay evaluation using an SEM is executed based on the recipe. The overlay evaluation result may be arbitrarily displayed in a list 1225 or the displays 1226, 1228, and 1231 as described above.

Figure 13:
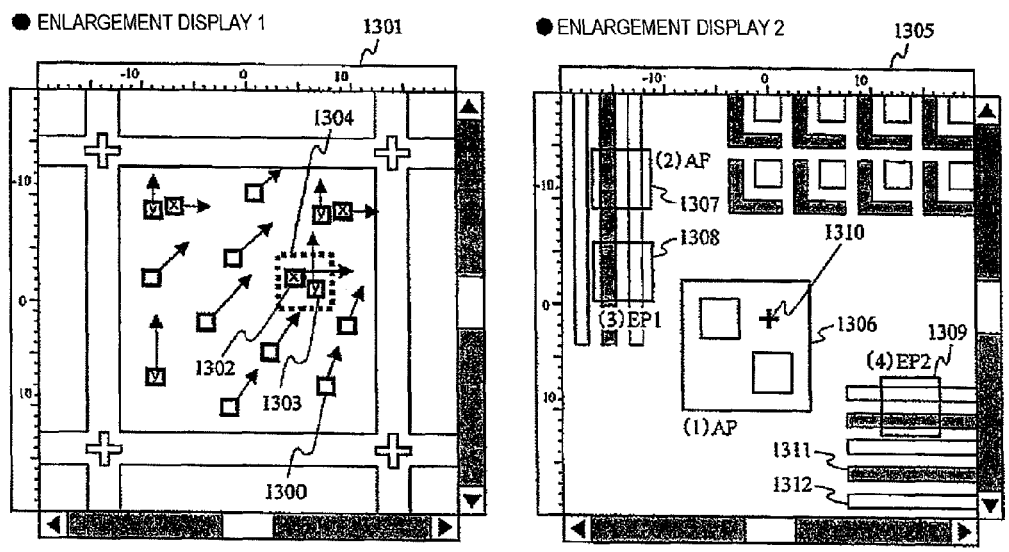
FIG. 13 is a diagram illustrating a GUI according to the present invention.

In FIG. 13, displays 1301 and 1305 are another display variations corresponding to the displays 1228 and 1231 in FIG. 12. In the display 1301, an EP is obtained according to an overlay evaluable direction, an EP (for example, 1300) indicated by a white square is an EP (EPXY) in which the overlay deviation in the x and y directions can be evaluated, an EP (for example, 1302) in which "x" is written in a square is an EP (EPX) in which only the overlay deviation in the x direction can be evaluated, and an EP (for example, 1303) in which "y" is written in a square is an EP (EPY) in which only the overlay deviation in the y direction can be evaluated. After the overlay deviation amount is measured, the deviation amount can be displayed using a vector, but, for example, a vector obtained in the EPX 1302 is only the deviation amount in the x direction (an arrow extending from the thick frame 1302 in the x direction). However, when an EPX and an EPY are closely exist such as 1302 and 1303, deviation vectors in the x and y directions can be approximately calculated based on the deviation amounts of both the EPX and the EPY and displayed. Further, the display 1305 enlarges and displays a range 1304. In this display, the first patterns are indicated by patterns (for example, 1311) hatched by oblique lines, the second patterns are indicated by white patterns (for example, 1312), and two EPs, that is, EP1 (denoted by 1308 and corresponding to 1302), EP2 (denoted by 1309 and corresponding to 1303) and the imaging sequence for imaging the two EPs are displayed. In this example, after the vertical incident position of electron beams are moved to move coordinates 1310 by the stage shift, movement of the field of view to an AP 1306 by the image shift and addressing are performed, and then movement of the field of view to an AP 1307 by the image shift and auto-focusing are performed. Thereafter, the field of view is moved to the EP1 (1308) by the image shift, imaging is performed, then the field of view is moved to the EP2 (1309) by the image shift, and imaging is performed. In FIG. 13, the imaging sequence is written as numbers (1) to (4) written before notations of AP, AF, EP1, and EP2. As described above, when the EP1 and the EP2 are included in the image shift allowable range, addressing and auto-focusing are performed only once for both EPs without performing addressing and auto-focus for each EP, and thus an imaging period of time can be saved. The imaging period of time can be one of determination information for EP decision. Such imaging sequence optimization between EPs can be performed in step 107 of FIG. 1, but imaging sequence optimization can be additionally performed between step 111 and step 112. It is because there are cases in which at the time of final EP decision of step 111, EP addition or deletion can be performed on a group of EP candidates assumed in step 107, and there are cases in which a setting of the imaging sequence among EPs changes, for example, single addressing is performed for all EPs.

Figure 14:
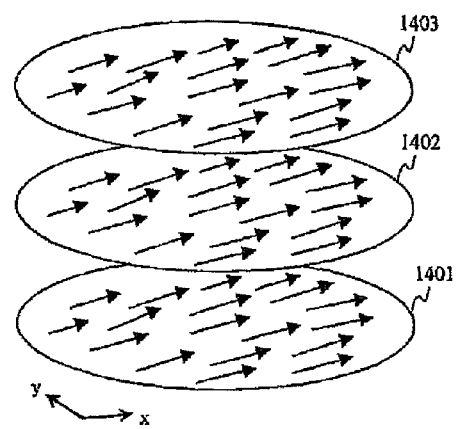
FIG. 14 is a diagram illustrating a GUI according to the present invention.

In the present invention, the overlay evaluation may be performed such that imaging is performed multiple times at different manufacturing process timings in the same wafer. FIG. 14 illustrates a display example of the result. FIG. 14 illustrates an overlay evaluation result among three or more layers, and an in-plane distribution of overlay deviation vectors of first patterns formed on a first layer and second patterns formed on a second layer is denoted by 1401, an in-plane distribution of overlay deviation vectors of the second patterns, and third patterns formed on a third layer is denoted by 1402, and an in-plane distribution of overlay deviation vectors of the third patterns and fourth patterns formed on a fourth layer is denoted by 1403. For example, an evaluation result of a display 1401 is considered to be obtained based on an image obtained by imaging a wafer directly after the second pattern is formed, an evaluation result of a display 1402 is considered to be obtained based on an image obtained by imaging a wafer directly after the third pattern is formed, and an evaluation result of a display 1403 is considered to be obtained based on an image obtained by imaging a wafer directly after the fourth pattern is formed. The displays 1401 to 1403 can be simultaneously displayed according to coordinates. Further, even when the displays 1401 to 1403 may be the same or different in an EP setting position, but of course, it is not guaranteed that an overlay evaluable EP is present at the same position regardless of the layers. Similarity in EP position between the layers may be used as one of determination criteria for the EP selection.

Figure 22:
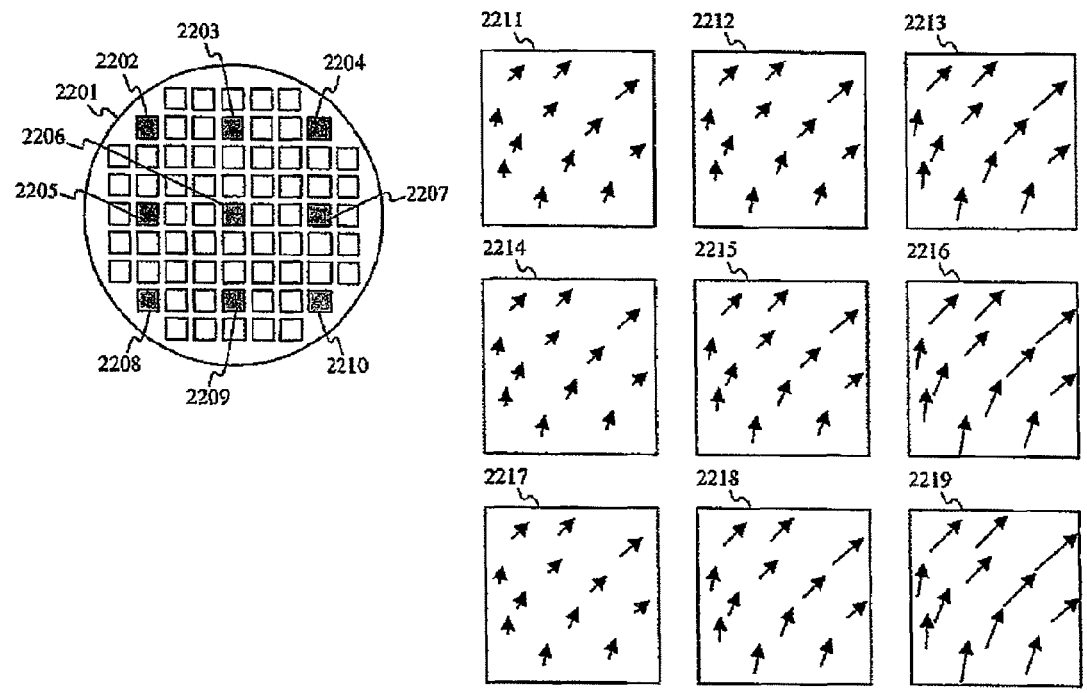
FIG. 22 is a diagram illustrating a distribution of a deviation vector in a wafer plane, a shot, or a chip plane.

In the present invention, a result of evaluating the overlay deviation in the wafer plane as well as overlay deviation evaluation in a shot or a chip can be displayed. In a left view of FIG. 22, a wafer 2201 is displayed, and a plurality of chips are arranged on the wafer 2201 (for example, chips 2202 to 2210). The overlay deviation in a chip may be evaluated for all chips, and for example, only the chips 2202 to 2210 indicated by oblique lines may be subjected to sampling and evaluated at a point of view of an inspection throughput. In a right view of FIG. 22, a distribution of deviation vectors in the chips measured in the chips 2202 to 2210 is displayed. Displays 2211 to 2219 correspond to displays of deviation vector distributions in the chips 2202 to 2210, and the deviation distributions can be displayed in parallel.

4. System Configuration

An example of a system configuration according to the present invention will be described with reference to FIGS. 15(*a*) and 15(*b*).

Figure 15:
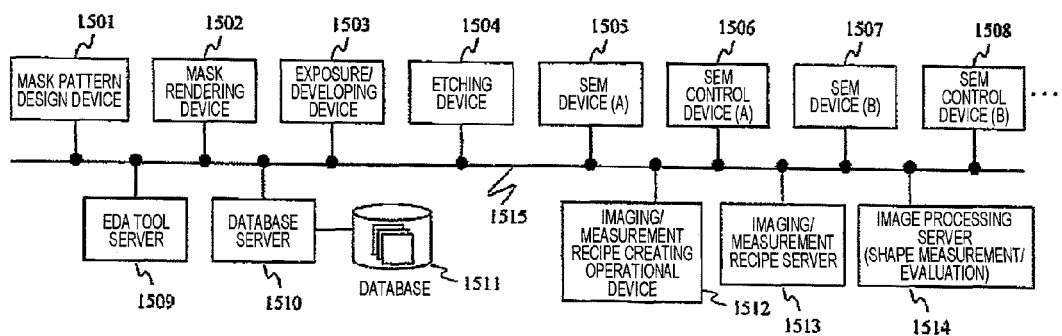
FIGS. 15(a) and 15(b) are diagrams illustrating a configuration of a device system for implementing the present invention.
Figure 15:
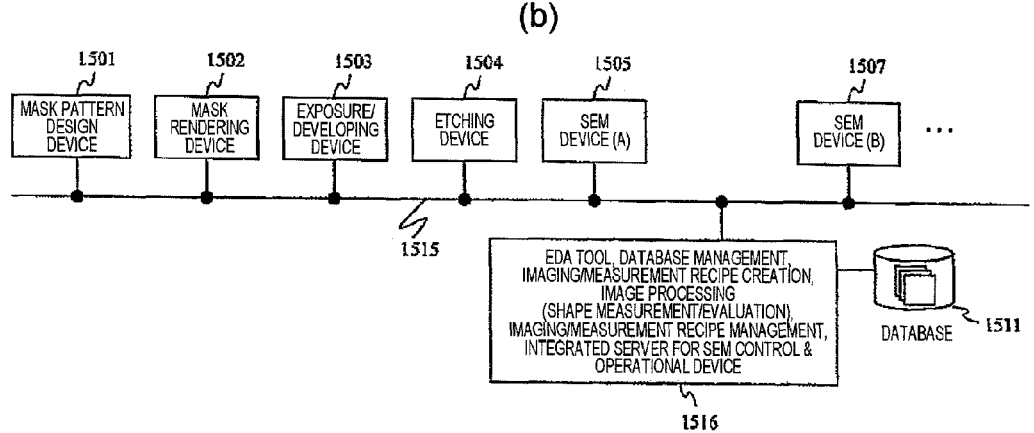

In FIG. 15(*a*), 1501 denotes a mask pattern design device, 1502 denotes a mask rendering device, 1503 denotes an exposure/developing device on a wafer of a mask pattern, 1504 denotes a wafer etching device, 1505 and 1507 denote SEM devices, 1506 and 1508 denote SEM control devices controlling the SEM devices, 1509 denotes an EDA tool server, 1510 denotes a database server, 1511 denotes a storage storing a database, 1512 denotes an imaging/measurement recipe creating device, 1513 denotes an imaging/ measurement recipe server, 1514 denotes an image processing device or an image processing server that perform pattern shape measurement and evaluation, and these devices can perform transmission and reception of information via a network 1515. The storage 1511 is attached to the database server 1510, and the database server 1510 may store and share some or all of (A) design data (mask design data (the absence/presence of optical proximity correction (OPC)) and design data of a wafer transfer pattern), (B) a simulation shape of an actual pattern estimated from the mask design data by a lithography simulation or the like, (C) generated imaging/measurement recipe, (D) imaged image (an OM image and an SEM image), (E) imaging and evaluation results (a measurement value of a pattern shape of each portion of an evaluation pattern, a pattern contour, a deformation amount of a pattern, an overlay deviation amount or deviation direction between patterns, normality or abnormality of an overlay position, or the like), and (F) a decision rule of an imaging/measurement recipe in association with a kind, a manufacturing process, a date and time, a data acquiring device, or the like. Further, in FIG. 15(*a*), as an example, the two SEM devices 1505 and 1507 are connected to the network, but in the present invention, the imaging/measurement recipe in an arbitrary number (two or more) of SEM devices can be shared with the database server 1510 or the imaging/measurement recipe server 1513. The plurality of SEM devices can be operated by single imaging/measurement recipe creation. Further, as the database is shared among a plurality of SEM devices, success/ failure or failure factors of the imaging or measurement in the past can be rapidly accumulated, and it can help create the excellent imaging/measurement recipe with reference to the factors.

FIG. 15(*b*) illustrates an example in which 1506, 1508, 1509, 1510, and 1512 to 1514 in FIG. 15(*a*) are integrated in a single device 1516. As in this example, arbitrary functions may be undertaken by an arbitrary number (two or more) of devices or integrated and processed.

According to the present invention, through the above-described technique, it is possible to understand a close in-plane distribution of overlay positions in a semiconductor device or the like using a scanning charged particle microscope. According to the present invention, it is possible to automatically create a recipe (setting of an evaluation point, an imaging sequence, and a measurement point/processing method) satisfying measurement requirements at a high speed, and it can be expected that an inspection preparation period of time (recipe creation period of time) is reduced, and an operator skill is unnecessary.

Further, in this specification, the description has been made in connection with the example of selecting an EP in a chip (for example, the chips 1601, 2101, and 2202 to 2210), but the chips may be replaced with shots (in other words, the shots 1601, 2101, and 2202 to 2210 are considered). Generally, a plurality of chips are included in a single shot. A shot refers to an area exposed by single exposure radiation, and when characteristics of an exposure device or the like are analyzed, it is effective to evaluate an overlay deviation distribution in a shot.

The present invention is not limited to the above embodiments, and includes various modified examples. For example, the above embodiment have been described in detail to help understand the present invention, and the present invention is not limited to an embodiment necessarily including all configuration described above. Further, some components in a certain embodiment may be replaced with components in another embodiment, and components in another embodiment may be added to components in a certain embodiment. For some components in each embodiment, addition, deletion, and replacement of another component can be performed.

Further, some or all of the above-described components, functions, processing units, and processing techniques may be implemented by hardware, for example, such that they are designed as integrated circuits. Further, the above-described components, functions, or the like may be implemented by software such that a processor interprets and executes a program for implementing the functions. Information such as a program, a table, or a file for implementing each function may be stored in a recording device such as a memory, a hard disk, a solid state drive (SSD) or a recording medium such as an IC card, an SD card, or a DVD.

Further, a control line or an information line has been described to be necessary, but all control lines or information lines are not necessarily included in products. Practically, almost all the components may be considered to be connected to each other.

REFERENCE SIGNS LIST 200 x-y-z coordinate system (coordinate system of electron optical system)
201 semiconductor wafer
202 electron optical system
203 electron gun
204 electron beam (primary electron)
205 condenser lens
206 deflector
207 ExB deflector
208 objective lens
209 secondary electron detector
210 and 211 back-scattered electron detector
212 to 214 and 215 processing/control unit
216 CPU
217 image memory
218 and 225 processing terminal
219 stage controller
220 deflection control unit
221 stage
222 recipe creating unit
223 imaging recipe creating device
224 measurement recipe creating device
226 database server
227 database (storage)
301 to 306 incident direction of convergent electron beam
307 sample surface
308 Ix-Iy coordinate system (image coordinate system)
309 image
416 wafer
417 to 420 chip in which alignment is performed
421 chip
422 OM alignment pattern imaging range
423 auto-focus pattern imaging range for SEM alignment pattern imaging
424 SEM alignment pattern imaging range
425 range in which part of design data is enlarged
426 MP
427 image shift allowable range from MP
428 AF
429 AP
430 AF
431 AST
432 ABCC
433 EP
501, 513, 515, 527 first pattern
502, 503, 514, 516, 517, and 526 second pattern
504, 518, 522, 528, 529, 531, 534, and 535 measurement point
505 and 519 EP
506 and 520 AP
507 distance between EP and AP
508 and 509 expected maximum imaging deviation
510, 511, and 521 distance between first and second patterns
512 actual EP imaging position
523, 524, 530, and 532 pattern center
525 and 533 distance between pattern centers
602, 606, 610, and 613 first pattern
603, 607, 611, and 614 second pattern
601, 605, 609, and 612 EP
604 and 608 measurement point
701 and 705 first pattern
702 and 706 second pattern
703, 707, 709, and 715 EP
704, 708, 710, 712, 716, and 718 measurement point
711, 713, 717, and 719 middle points of left and right edges
714 and 720 distance between middle points of left and right edges
721 to 724 edge position
802, 803, 808, and 811 first pattern
805, 807, and 810 second pattern
801 and 806 EP
804 and 809 edge position
901, 905, 914, and 919 chip
902, 906, 915, and 920 overlay evaluation-dedicated pattern
904, 908, 910, 911, 913, 916, 917, 921, 922, and 923 EP
900, 903, 907, 909, and 912 EP arrangeable area
918, 924, and 925 distance between EPs
926 area in which EP is to be arranged
1002, 1004, and 1012 first pattern
1003, 1005, 1006, and 1013 second pattern
1001, 1007, and 1008 EP
1009 AP
1010 and 1011 distance between EP and AP
1102 and 1107 first pattern
1103 and 1108 second pattern
1101 and 1106 EP
1104, 1105, and 1109 measurement point
1110 edge position
1111 brightness profile
1501 mask pattern design device
1502 mask rendering device
1503 exposure/developing device
1504 etching device
1505 and 1507 SEM device
1506 and 1508 SEM control device
1509 EDA tool server
1510 database server
1511 database
1512 imaging/measurement recipe creating operational device
1513 imaging/measurement recipe server
1514 image processing server (shape measurement/evaluation)
1515 network
1516 EDA tool, database management, imaging/measurement recipe creation, image processing (shape measurement/evaluation), imaging/measurement recipe management, integrated server for SEM control & operational device
1601 chip
1602 to 1604 EP arrangeable area
1605 and 1606 EP
1607 and 1608 overlay deviation amount of each direction
1609 grid
1610 position in which overlay deviation is desired to be measured
1611 overlay deviation vector
1701, 1706, 1711, 1721, and 1723 first pattern
1702, 1707, 1712, 1720, and 1722 second pattern
1703, 1708, 1713, 1718, and 1719 EP
1704, 1705, 1709, 1710, 1714 to 1717, 1724, and 1725 measurement point
1726 oblique angle of oblique interconnection pattern
1727 x-y coordinate system (coordinate system of wafer, shot, or chip)
1728 Ix-Iy coordinate system (image coordinate system)
1801 to 1803 EP
1804 to 1806, 1811, 1813, 1815, 1818, and 1821 overlay deviation amount of each direction
1807 to 1809 straight line connecting EPs
1810, 1812, 1814, 1817, 1820, and 1827 position in which overlay deviation is desired to be measured
1816, 1819, 1822 distance between positions 1814, 1817, and 1820 in which overlay deviation is desired to be measured and straight line 1809
1823 to 1825 crossing point of vertical line from positions 1814, 1817, and 1820 in which overlay deviation is desired to be measured to straight line 1809 and straight line 1809
1826 grid
1828 to 1831 overlay deviation vector
1901 and 1902 first pattern
1903 to 1905 second pattern
1903a to 1905c, and 1903b to 1905b second pattern after cutting process
1906 pattern of cutting process
1907 edge formed by first manufacturing process
1908 edge formed by second manufacturing process
1909 edge formed by cutting process
1910 to 1915 measurement point
2001, 2003 first pattern
2002, 2004 second pattern
2005 hard mask layer
2005a to 2005h pattern masked by sidewall spacer
2006 base layer
2007 deposited layer
2007a to 2007h sidewall spacer
2008 to 2015 measurement point
2016 to 2019 pattern edge
2101 chip
2102 and 2105 EP arrangeable area
2103, 2104, 2106, and 2107 EP
2119 and 2120 actual EP imaging position
2108 distance between EPs
2109 and 2111 first pattern
2110 and 2112 second pattern
2113 to 2116 measurement point
2117, 2118 pattern center
2201 wafer
2202 to 2219 chip
2211 to 2219 distribution of overlay deviation vectors in chips 2202 to 2219

The invention claimed is:
1. A pattern evaluation method of evaluating an overlay position between a first pattern formed on a sample by a first manufacturing process and a second pattern formed on the sample by a second manufacturing process using an image obtained by imaging an evaluation point on the sample through a scanning charged particle microscope, the pattern evaluation method comprising:
a step of inputting pattern layout information and manufacturing process information;
a step of allocating information representing whether each pattern edge in the layout information is an edge formed by a manufacturing process based on the layout information and the manufacturing process information as attribute information; and
a step of deciding one or more evaluation points so that the edge formed by the first manufacturing process and the edge formed by the second manufacturing process are included in a field of view based on the attribute information.

2. The pattern evaluation method according to claim 1, wherein the manufacturing process includes a cutting process.

3. The pattern evaluation method according to claim 1, wherein the manufacturing process includes a process of forming a sidewall spacer.

4. The pattern evaluation method according to claim 1, wherein imaging deviation allowed to evaluate an overlay position on evaluation point candidates is estimated based on pattern layout information, an evaluation point is decided from among the evaluation point candidates, and an imaging sequence for imaging the evaluation point is decided based on the allowed imaging deviation, and
the allowed imaging deviation is estimated under a condition that it does not fail to specify the first pattern and the second pattern included in the evaluation point even when the imaging deviation occurs.

5. The pattern evaluation method according to claim 1, wherein in the step of deciding the evaluation point, deformation easiness of each portion of a pattern is evaluated based on the layout information, and an evaluation point is decided based on the deformation easiness of each portion.

6. The pattern evaluation method according to claim 1, wherein in the step of deciding the evaluation point, both right and left edges of a pattern when the overlay position in the x direction is evaluated or both upper and lower edges of a pattern when the overlay position in the y direction is evaluated are included within the evaluation point for each of the first pattern and the second pattern.

7. The pattern evaluation method according to claim 1, wherein when the first pattern is a lower layer pattern and the second pattern is an upper layer pattern in connection with stacked layers on a wafer, in the step of deciding the evaluation point, invisibility of the lower layer pattern by the upper layer pattern is estimated based on the layout information, and the evaluation point is decided in view of the invisibility, and
the estimating of the invisibility includes an estimation when the lower layer pattern is hidden as a pattern is deformed.

8. The pattern evaluation method according to claim 1, wherein in the step of deciding the evaluation point, a plurality of areas are set on the sample, and at least one evaluation point is decided in each of the areas.

9. The pattern evaluation method according to claim 1, wherein in the step of deciding the evaluation point, a condition related to a distance between two arbitrary evaluation points is given, and a plurality of evaluation points are decided to satisfy the condition.

10. The pattern evaluation method according to claim 1, wherein in the step of deciding the evaluation point, the evaluation point is decided by designating at least one or more evaluation points in advance, and searching another evaluation point including a pattern similar to a pattern included in the evaluation point based on the designated evaluation points.

11. The pattern evaluation method according to claim 1, wherein in the step of deciding the evaluation point, a measurement point used to evaluate the overlay position in the evaluation point is decided based on the pattern layout information.

12. The pattern evaluation method according to claim 1, wherein the step of deciding the evaluation point includes a process of deciding a processing method of evaluating an overlay position in the evaluation point based on the pattern layout information for each evaluation point, and alternatives of the processing method include at least a method of imaging the evaluation point, comparing an obtained image with design data, and evaluating an overlay position and a method of imaging the evaluation point, recognizing a pattern from an obtained image by image processing, and evaluating an overlay position.

13. The pattern evaluation method according to claim 1, wherein in the step of deciding the evaluation point, evaluation point candidates are displayed according to the attribute information of the evaluation point, and the attribute information includes a direction of an evaluable overlay position.

14. The pattern evaluation method according to claim 1, wherein when the overlay position in the x direction is evaluated, first and second evaluation points are decided so that at least one of right and left edges of the first pattern and one of right and left edges of the second pattern are included in the first evaluation point, and one of the right and left edges of the first pattern and one of the right and left edges of the second pattern are included in the second evaluation point, and the overlay deviation is evaluated using the first and second evaluation points, a direction of a pattern included in the first evaluation point and a direction of a pattern edge included in the second evaluation point are reversed right and left in the first and second patterns, when the overlay position in the y direction is evaluated, first and second evaluation points are decided so that at least one of upper and lower edges of the first pattern and one of upper and lower edges of the second pattern are included in the first evaluation point, and one of the upper and lower edges of the first pattern and one of the upper and lower edges of the second pattern are included in the second evaluation point, and the overlay deviation is evaluated using the first and second evaluation points, and a direction of a pattern included in the first evaluation point and a direction of a pattern edge included in the second evaluation point are upside down in the first and second patterns.

15. The pattern evaluation method according to claim 1, wherein in the step of deciding the evaluation point, a plurality of evaluation points in which a direction in which an overlay position is evaluable is set for each evaluation point are decided, and in the step of evaluating the overlay position, an overlay deviation vector at certain coordinates is calculated based on overlay deviation in a direction in which the overlay position is evaluable which is measured in each of the plurality of evaluation points.

16. A pattern evaluation device of evaluating an overlay position between a first pattern formed on a sample by a first manufacturing process and a second pattern formed on the sample by a second manufacturing process using an image obtained by imaging an evaluation point on the sample through a scanning charged particle microscope, the pattern evaluation device comprising:

a unit configured to input pattern layout information and manufacturing process information;

a unit configured to allocate information representing whether each pattern edge in the layout information is an edge formed by a manufacturing process based on the layout information and the manufacturing process information as attribute information; and a unit configured to decide one or more evaluation points so that the edge formed by the first manufacturing process and the edge formed by the second manufacturing process are included in a field of view based on the attribute information.

* * * * *